(12) United States Patent  
Bizzell et al.

(10) Patent No.: US 8,100,290 B2  
(45) Date of Patent: Jan. 24, 2012

(54) SPOOLED ADHESIVE BANDAGE DISPENSER

(75) Inventors: Daniel Lee Bizzell, Davidson, NC (US); David Berglund, Marvin, NC (US); Jerry Shew, Charlotte, NC (US); Carole Ruffin, Cleveland, OH (US); Ian Kovacevich, Charlotte, NC (US)

(73) Assignee: Edison Nation, LLC, Charlotte, NC (US)

( * ) Notice: Subject to any disclaimer, the term of this patent is extended or adjusted under 35 U.S.C. 154(b) by 401 days.

(21) Appl. No.: 12/397,343

(22) Filed: Mar. 3, 2009

(65) Prior Publication Data

US 2009/0218364 A1    Sep. 3, 2009

Related U.S. Application Data

(60) Provisional application No. 61/033,310, filed on Mar. 3, 2008.

(51) Int. Cl.  
*A61F 15/00* (2006.01)

(52) U.S. Cl. .............. 221/25; 221/73; 221/74; 221/72; 221/42; 156/577; 225/16

(58) Field of Classification Search .......... 221/25, 221/70–73, 724; 156/577; 225/16  
See application file for complete search history.

(56) References Cited

U.S. PATENT DOCUMENTS

| | | | |
|---|---|---|---|
| 2,005,676 A | 6/1935 | Hanover | |
| 2,068,703 A | 1/1937 | Powdermaker | |
| 2,133,609 A | 10/1938 | Eustis | |
| 2,391,301 A | 12/1945 | Dukehart, Jr. | |
| 2,432,541 A | 12/1947 | Peck | |
| 2,464,426 A | 3/1949 | Williams | |
| 2,721,550 A | 10/1955 | Banff | |
| 2,793,745 A | 5/1957 | Cox, Jr. | |
| 3,189,219 A | 6/1965 | Holtzworth et al. | |
| 3,245,855 A | 4/1966 | Stenvall | |
| 3,530,494 A | 9/1970 | Baratta | |

(Continued)

FOREIGN PATENT DOCUMENTS

JP        03027309 B2    1/2000

(Continued)

OTHER PUBLICATIONS

"International Search Report" and "Written Opinion of the International Search Authority" (Korean Intellectual Property Office) in Edison Nation, LLC et al. on Jul. 15, 2009, for International Patent Application Serial No. PCT/US2009/035941 filed Mar. 3, 2009, 8 pages.

(Continued)

*Primary Examiner* — Mark A Deuble  
(74) *Attorney, Agent, or Firm* — Tillman Wright, PLLC; James D. Wright; Chad D. Tillman

(57) ABSTRACT

A spooled adhesive bandage dispenser includes a case, a replaceable cartridge and an activation wheel. The cartridge is disposed within the case and includes a bandage roll and a waste core. The bandage roll includes a strip of bandage packages sealed between two strips of packaging. The activation wheel is at least partially exposed outside the case. By rotating the activation wheel, the packaging strips are pulled apart and the bandage package is forced out of the case through a slot. At the same time, the packaging strips are wound around the waste core. When the bandage roll is gone, the entire cartridge may be replaced.

17 Claims, 36 Drawing Sheets

U.S. PATENT DOCUMENTS

| | | | |
|---|---|---|---|
| 3,612,265 A | 10/1971 | Dickerson | |
| 3,835,992 A | 9/1974 | Adams, IV | |
| 3,899,077 A | 8/1975 | Spiegelberg | |
| 4,167,253 A | 9/1979 | Rutz | |
| 4,413,621 A | 11/1983 | McCracken et al. | |
| 4,512,462 A | 4/1985 | Dills | |
| 4,549,653 A | 10/1985 | Lauritzen | |
| 4,666,040 A | 5/1987 | Murata | |
| 4,727,616 A | 3/1988 | Kucera et al. | |
| 4,735,342 A | 4/1988 | Goldstein | |
| 4,751,133 A | 6/1988 | Szycher et al. | |
| 4,807,613 A | 2/1989 | Koehnke et al. | |
| 4,807,753 A | 2/1989 | Goldstein | |
| 4,832,008 A | 5/1989 | Gilman | |
| 4,858,604 A | 8/1989 | Konishi | |
| 4,917,929 A | 4/1990 | Heinecke | |
| 4,993,586 A | 2/1991 | Taulbee et al. | |
| 5,065,894 A | 11/1991 | Garland | |
| 5,133,477 A | 7/1992 | Etheredge, III et al. | |
| 5,213,565 A | 5/1993 | Rollband | |
| 5,271,522 A | 12/1993 | Ko et al. | |
| 5,310,402 A | 5/1994 | Rollband | |
| 5,358,140 A | 10/1994 | Pellegrino | |
| 5,511,689 A | 4/1996 | Frank | |
| 5,533,962 A | 7/1996 | Peterman et al. | |
| 5,543,270 A | 8/1996 | Akao et al. | |
| 5,690,610 A | 11/1997 | Ito et al. | |
| 5,782,786 A | 7/1998 | Tomaiuolo | |
| 5,792,092 A | 8/1998 | Turngren | |
| 5,806,713 A * | 9/1998 | Dudley et al. | 221/73 |
| 5,938,070 A * | 8/1999 | Welborn et al. | 221/73 |
| 5,981,823 A | 11/1999 | Turngren | |
| 6,010,002 A | 1/2000 | Petterson | |
| 6,014,788 A | 1/2000 | Jaffri | |
| 6,053,318 A | 4/2000 | Petterson | |
| 6,120,792 A | 9/2000 | Juni | |
| 6,213,343 B1 | 4/2001 | Damikolas | |
| 6,297,422 B1 | 10/2001 | Hansen et al. | |
| 6,299,018 B1 | 10/2001 | Kimball | |
| 6,439,289 B1 * | 8/2002 | Schlotthauer | 156/539 |
| D472,319 S | 3/2003 | Oltmann | |
| 6,592,889 B1 | 7/2003 | Stout et al. | |
| 6,617,486 B1 | 9/2003 | Murata | |
| 6,641,081 B2 | 11/2003 | Huang | |
| 6,719,137 B2 | 4/2004 | Dotta | |
| 6,755,321 B2 | 6/2004 | Solovay et al. | |
| 6,756,519 B2 | 6/2004 | Johnson et al. | |
| 7,012,170 B1 | 3/2006 | Tomaiuolo | |
| 7,568,580 B2 * | 8/2009 | Fenton | 206/390 |
| 7,683,235 B2 * | 3/2010 | Wendorf | 602/57 |
| 2002/0170918 A1 | 11/2002 | Solovay et al. | |
| 2003/0047566 A1 | 3/2003 | DeVita | |
| 2003/0204158 A1 | 10/2003 | Johnson et al. | |
| 2005/0167542 A1 | 8/2005 | Lehse | |

FOREIGN PATENT DOCUMENTS

| | | |
|---|---|---|
| KR | 200345291 Y1 | 3/2004 |
| KR | 200407336 Y1 | 1/2006 |
| WO | 9924341 A1 | 5/1999 |
| WO | 02091978 A2 | 11/2002 |
| WO | 03063750 A1 | 8/2003 |
| WO | 2009111517 A1 | 9/2009 |

OTHER PUBLICATIONS

Tomaiuolo, Theodore, Speed Bandage, Sales Flyer, Jan. 20, 2007, 2 pages, Plainville, CT.

* cited by examiner

SPOOLED ADHESIVE BANDAGE DISPENSER

CROSS-REFERENCE TO RELATED APPLICATION

The present application is a U.S. nonprovisional patent application of, and claims priority under 35 U.S.C. §119(e) to, U.S. provisional patent application Ser. No. 61/033,310, filed Mar. 3, 2008, which provisional patent application is incorporated by reference herein.

COPYRIGHT STATEMENT

All of the material in this patent document is subject to copyright protection under the copyright laws of the United States and of other countries. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE PRESENT INVENTION

1. Field of the Present Invention

The present invention relates generally to product packaging, and, in particular, to a spooled adhesive bandage dispenser.

2. Background

Conventional self-adhesive bandages are typically packaged individually in a paper wrapper. Frequently, it is difficult to remove the bandage from the paper wrapper, remove the release liner from the adhesive and apply the bandage, especially in urgent care situations. A roll dispenser for self-adhesive bandages has been proposed to make the process of dispensing and applying a bandage more convenient. An example of such a dispenser is shown and described in commonly-assigned U.S. Pat. No. 5,782,786, the entirety of which is incorporated herein by reference.

A problem with adhesive bandages dispensed from a roll, which is a problem shared by many other products dispensed in a similar manner, is locating and grasping the end of the roll in order to dispense the next bandage. Typically, the consumer must feel around the circumference of the roll to locate the end of the roll and then lift the end with a fingernail. Various tab arrangements have been proposed in a context of other products to facilitate finding and lifting the end of a rolled adhesive product. Such arrangements are shown, for example, in U.S. Pat. Nos. 4,512,462; 4,727,616 and 6,014,788. A further arrangement is proposed in commonly-assigned U.S. Pat. No. 6,756,519, the entirety of which is incorporated herein by reference.

A further problem with adhesive bandage rolls is the need for a user to utilize both hands to remove a bandage or bandage package from the roll.

Thus, a need exists for a simple, convenient way to store adhesive bandage packages until needed and then dispense individual bandages or bandage packages easily for immediate use.

SUMMARY OF THE PRESENT INVENTION

The present invention comprises a spooled adhesive bandage dispenser.

Broadly defined, the present invention according to one aspect is a spooled adhesive bandage dispenser, including: a case; a bandage roll disposed at least partially in the case and having a plurality of bandages connected together in end-to-end relationship; an activation wheel, at least partially exposed outside the case, for causing a bandage to be forced out of the case; and a waste core disposed at least partially within the case and in operative connection with the activation wheel, wherein the activation wheel is configured to receive and wind at least one waste strip from the bandage roll as an exposed bandage is forced out of the case.

In a feature of this aspect, the spooled adhesive bandage dispenser further includes a take-up reel assembly, disposed at least partially within the case, for receiving and winding at least one waste strip from the bandage roll as an exposed bandage is forced out of the case.

In another feature of this aspect, the spooled adhesive bandage dispenser further includes at least two waste guides, disposed adjacent and partially surrounding the bandage roll, for guiding waste strips from the bandage roll to the waste core as an exposed bandage is forced out of the case. In a further feature, each waste guide defines a waste channel within the case, thereby providing an uninterrupted path to the waste core for waste strips unwound from the bandage roll.

In another feature of this aspect, the spooled adhesive bandage dispenser further includes a nosepiece disposed generally between the bandage roll and an exit slot of the case through bandages exit from the case, wherein the nosepiece is adapted for guiding waste strips from the bandage roll to the waste core as an exposed bandage is forced out of the case.

In another feature of this aspect, the bandage roll is contained on a replaceable cartridge.

In another feature of this aspect, the case is made of molded plastic.

In another feature of this aspect, the waste core is made from a biodegradable material.

In another feature of this aspect, the activation wheel includes two spaced apart activation wheels, each wheel being rotatably attached to a side of the case such that their rotation relative to the case occurs about a common axis of rotation.

In another feature of this aspect, the activation wheel includes a gripping band arranged about the perimeter thereof.

In another feature of this aspect, the spooled adhesive bandage dispenser further includes a latch to facilitate opening the case.

Broadly defined, the present invention according to another aspect is a spooled adhesive bandage dispenser, including: a case; a bandage roll disposed at least partially in the case; and a take-up reel assembly, disposed at least partially within the case, for receiving and winding at least one waste strip from the bandage roll as an exposed bandage is forced out of the case.

In a feature of this aspect, the take-up reel assembly includes at least one activation wheel at least partially exposed outside the case, each of the at least one wheel being rotatably attached to a side of the case such that its rotation relative to the case occurs about a common axis of rotation, wherein rotation of the at least one activation wheel forces an exposed bandage out of the case. In a further feature, the take-up reel assembly includes a waste core disposed at least partially within the case and in operative connection with the activation wheel, wherein the activation wheel is configured to receive and wind at least one waste strip from the bandage roll as an exposed bandage is forced out of the case.

In another feature of this aspect, the take-up reel assembly includes at least two waste guides, disposed adjacent and partially surrounding the bandage roll, for guiding waste strips from the bandage roll to the waste core as an exposed bandage is forced out of the case.

In another feature of this aspect, the bandage roll is contained on a replaceable cartridge.

In another feature of this aspect, the case is made of molded plastic.

Broadly defined, the present invention according to another aspect is a spooled adhesive bandage dispenser, including: a case; a bandage roll disposed at least partially in the case; and at least two waste guides, disposed adjacent and partially surrounding the bandage roll, for guiding waste strips from the bandage roll as an exposed bandage is forced out of the case.

In a feature of this aspect, the take-up reel assembly includes at least one activation wheel at least partially exposed outside the case, each of the at least one activation wheel being rotatably attached to a side of the case such that its rotation relative to the case occurs about a common axis of rotation, wherein rotation of the at least one activation wheel forces an exposed bandage out of the case.

In another feature of this aspect, the bandage roll is contained on a replaceable cartridge.

Broadly defined, the present invention according to another aspect is a spooled adhesive bandage dispenser, including: a case; a bandage roll disposed at least partially in the case; and a waste core, disposed at least partially within the case, for receiving and winding at least one waste strip from the bandage roll as an exposed bandage is forced out of the case.

In a feature of this aspect, the take-up reel assembly includes at least one activation wheel at least partially exposed outside the case, each of the at least one activation wheel being rotatably attached to a side of the case such that its rotation relative to the case occurs about a common axis of rotation, wherein rotation of the at least one activation wheel forces an exposed bandage out of the case. In a further feature, the waste core is disposed in operative connection with the activation wheel, wherein the activation wheel is configured to receive and wind at least one waste strip from the bandage roll as an exposed bandage is forced out of the case.

In another feature of this aspect, the spooled adhesive bandage dispenser further includes at least two waste guides, disposed adjacent and partially surrounding the bandage roll, for guiding waste strips from the bandage roll to the waste core as an exposed bandage is forced out of the case.

In another feature of this aspect, the bandage roll is contained on a replaceable cartridge.

In another feature of this aspect, the case is made of molded plastic.

Broadly defined, the present invention according to another aspect is a spooled adhesive bandage dispenser, including: a case; and a replaceable cartridge, including a bandage roll and a waste core.

In a feature of this aspect, the spooled adhesive bandage dispenser further includes a take-up reel assembly, disposed at least partially within the case, for receiving and winding at least one waste strip from the bandage roll as an exposed bandage is forced out of the case. In a further feature, the take-up reel assembly includes at least one activation wheel at least partially exposed outside the case, each of the at least one activation wheel being rotatably attached to a side of the case such that its rotation relative to the case occurs about a common axis of rotation, wherein rotation of the at least one activation wheel forces an exposed bandage out of the case. In a still further feature, the waste core is disposed in operative connection with the activation wheel, wherein the activation wheel is configured to receive and wind at least one waste strip from the bandage roll as an exposed bandage is forced out of the case.

In another feature of this aspect, the spooled adhesive bandage dispenser further includes at least two waste guides, disposed adjacent and partially surrounding the bandage roll, for guiding waste strips from the bandage roll to the waste core as an exposed bandage is forced out of the case.

In another feature of this aspect, the case is made of molded plastic.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, which are not necessarily to scale, wherein.

DETAILED DESCRIPTION OF THE PREFERRED EMBODIMENTS

Figure 1:
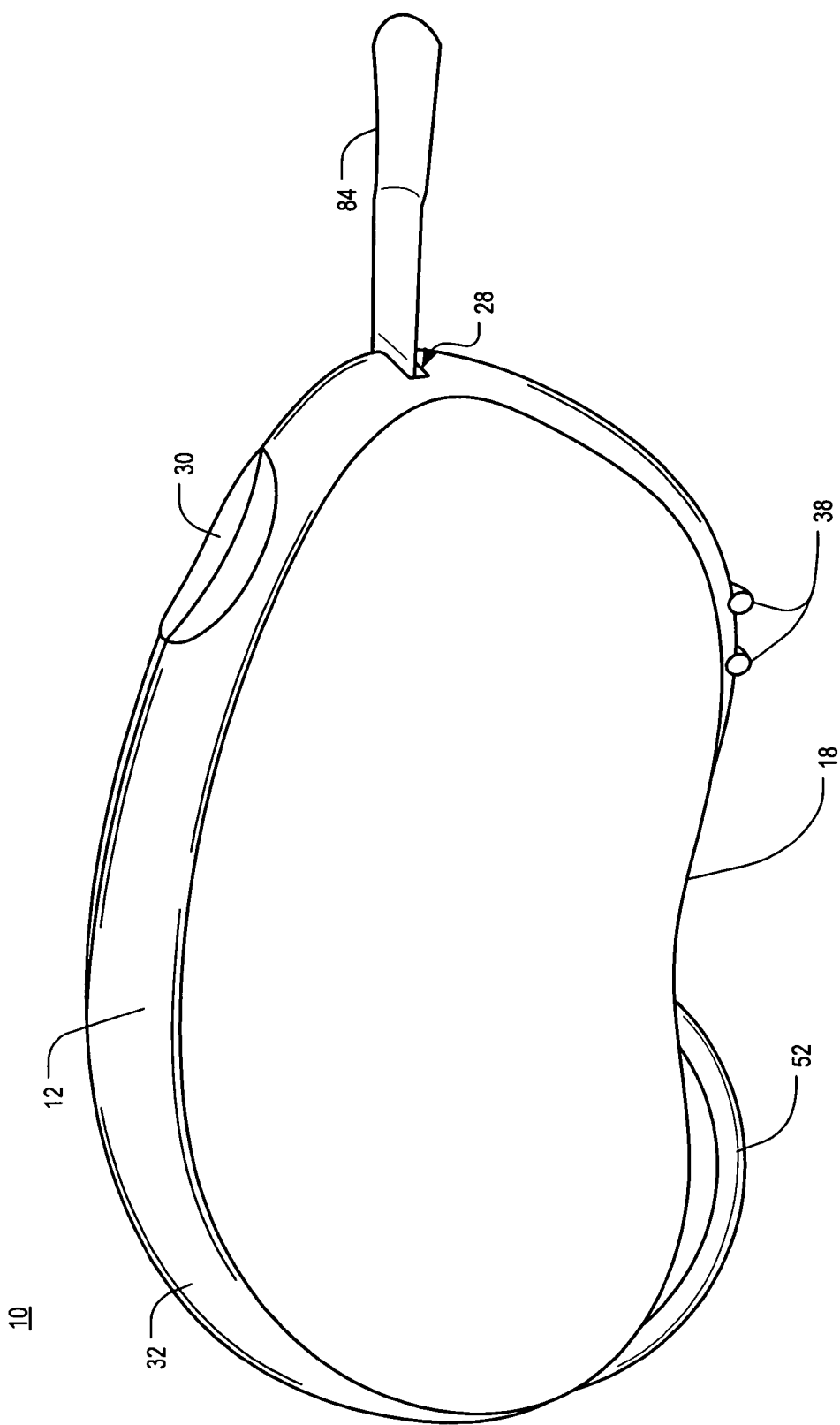
FIG. 1 is a right side perspective view of a spooled adhesive bandage dispenser in accordance with a first preferred embodiment of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, the preferred embodiments of the present invention are next described. The following description of the preferred embodiment(s) is merely exemplary in nature and is in no way intended to limit the invention, its application, or uses.

Figure 2:
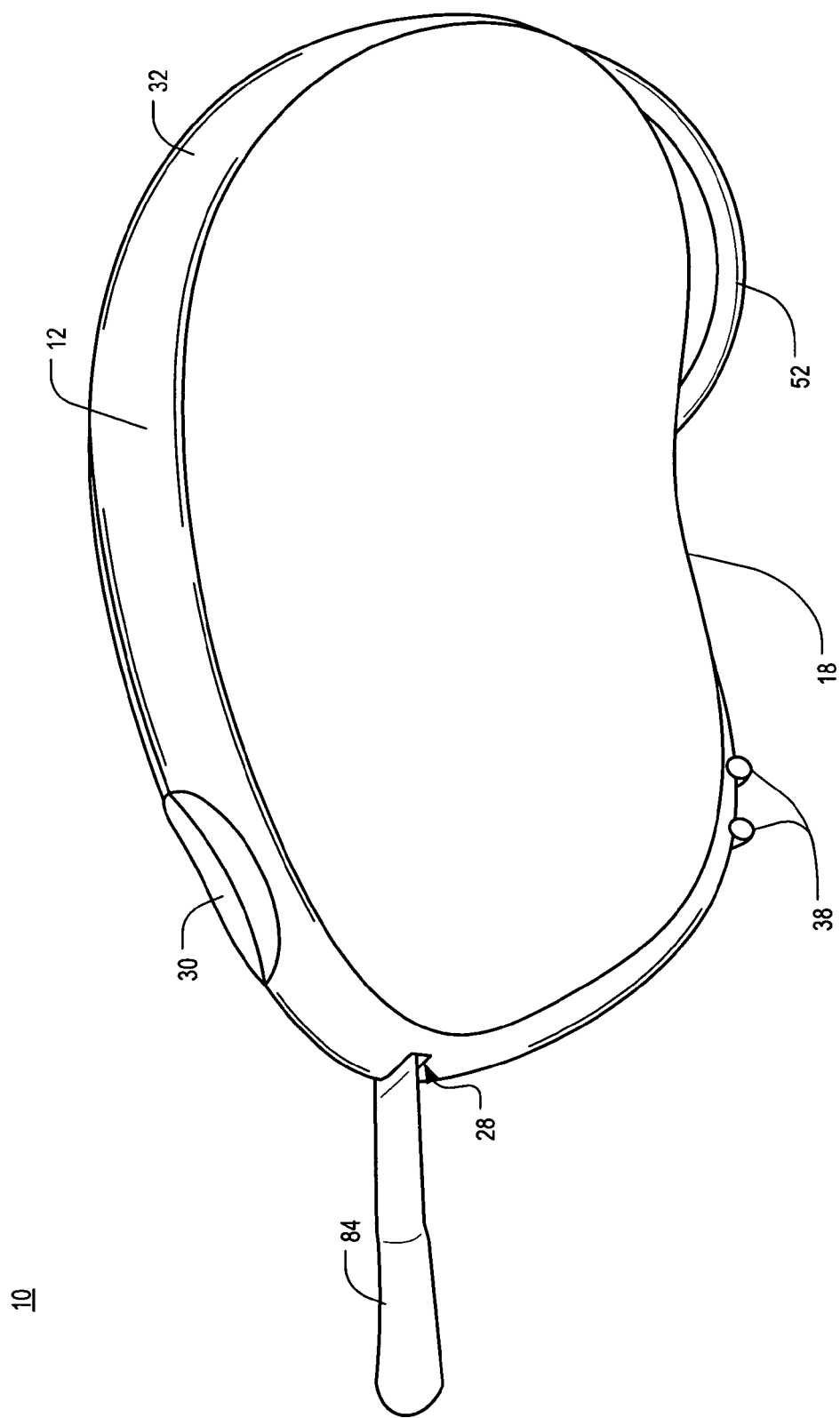
FIG. 2 is a left side perspective view of the spooled adhesive bandage dispenser of FIG. 1.
Figure 3:
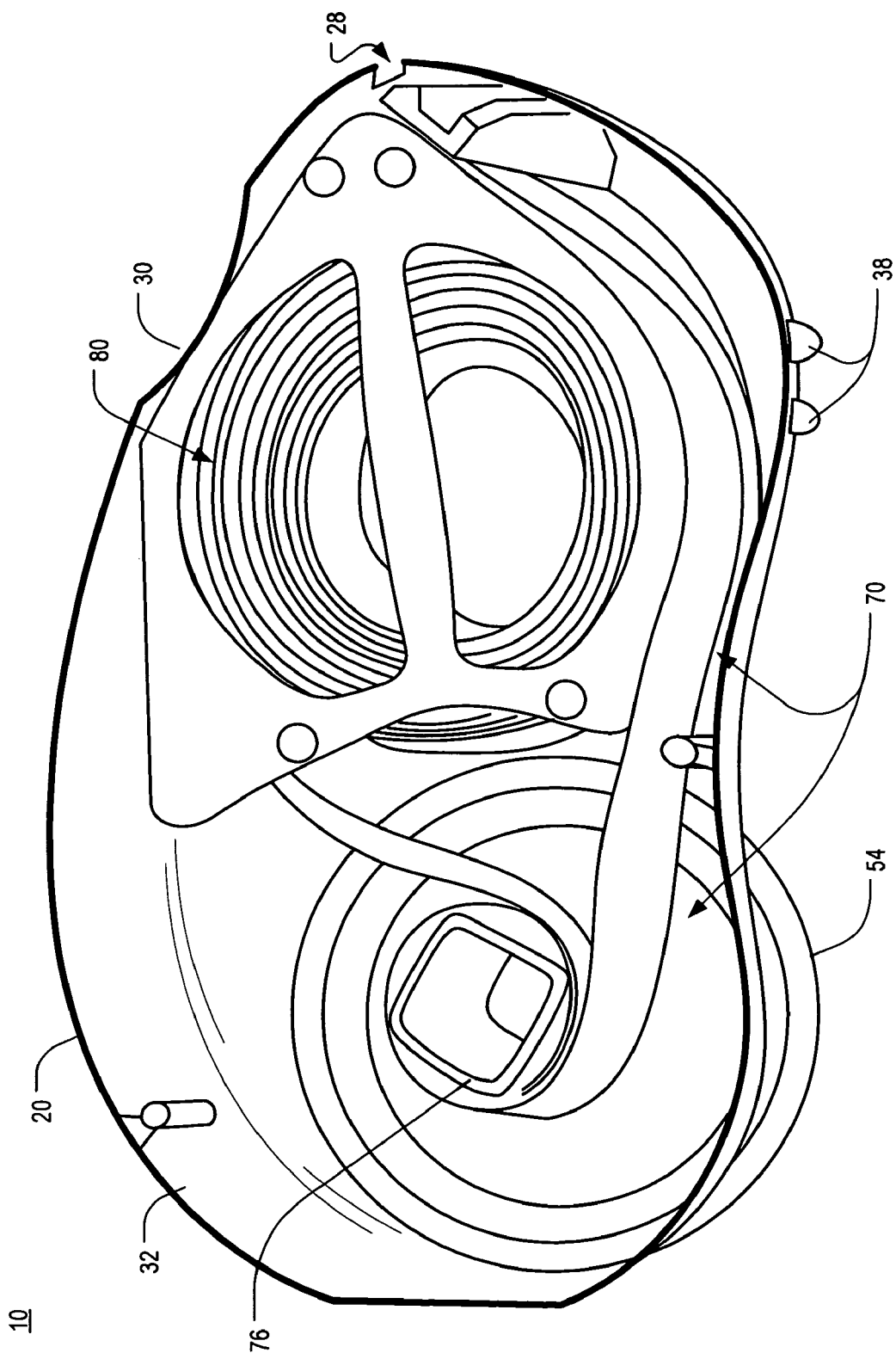
FIG. 3 is a perspective view of the spooled adhesive bandage dispenser of FIG. 1, shown with the right case half removed.
Figure 4:
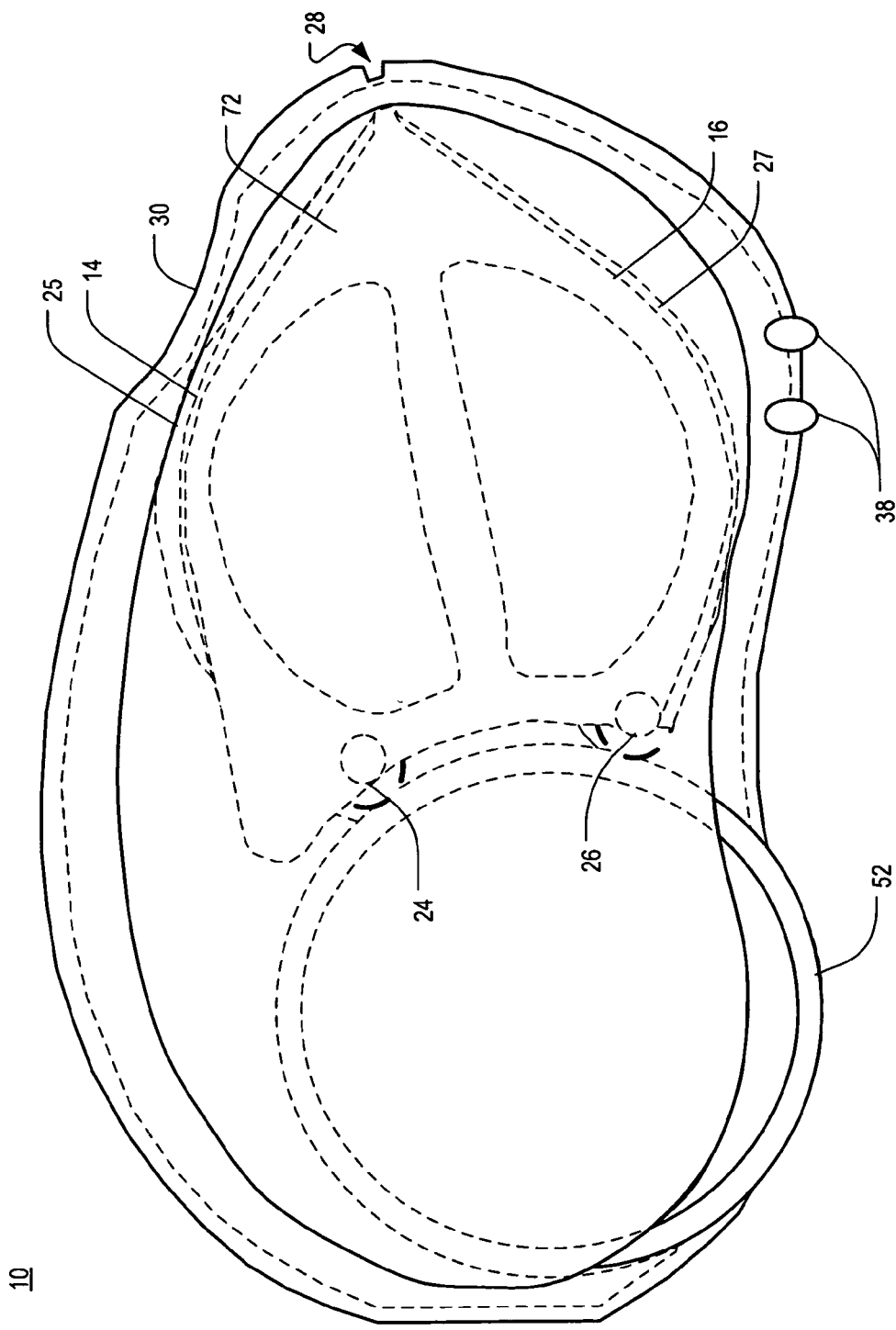
FIG. 4 is a perspective view of the right side of the spooled adhesive bandage dispenser of FIG. 1, shown with the bandage roll removed.
Figure 5:
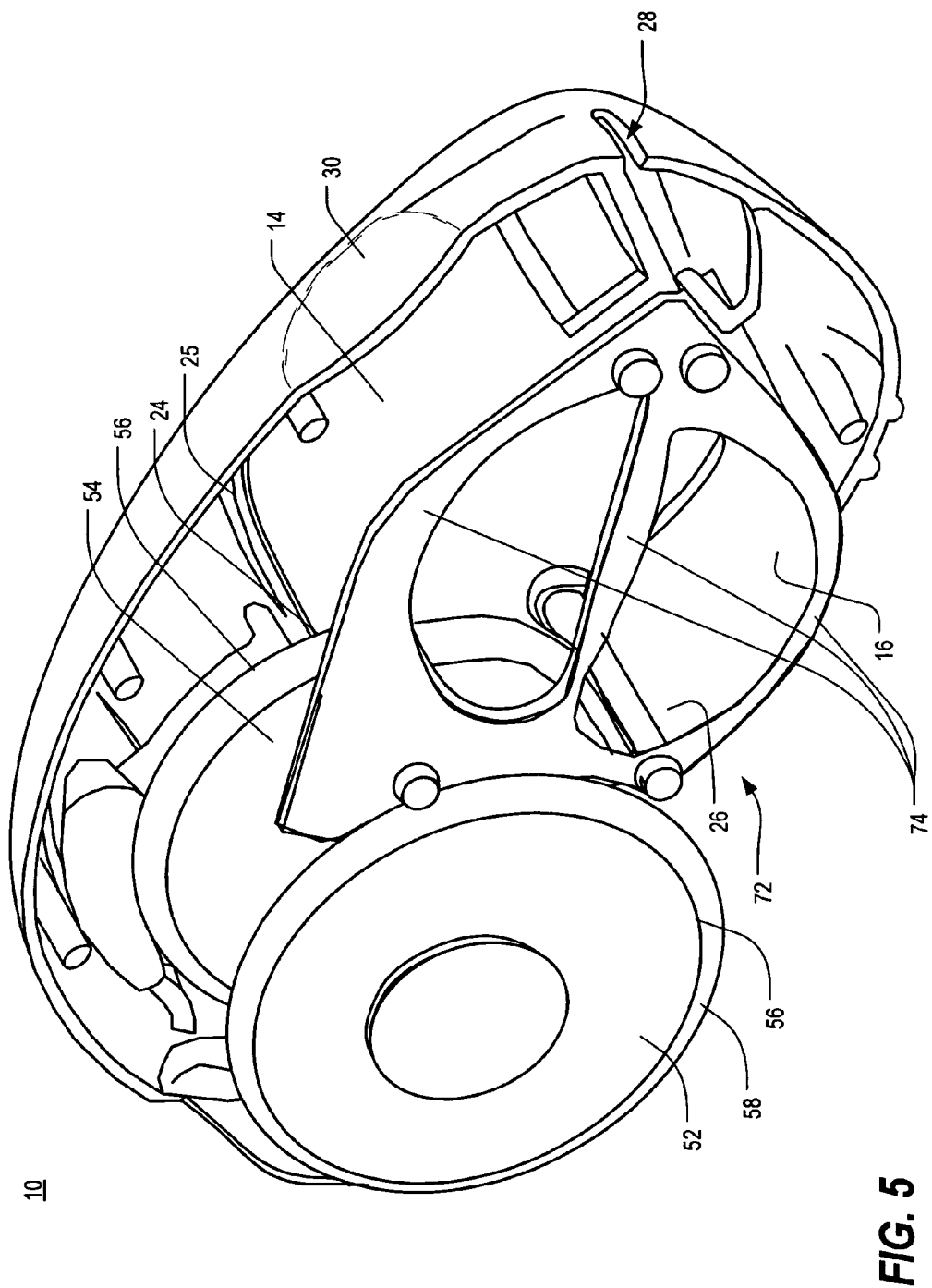
FIG. 5 is a perspective view of the right side of the spooled adhesive bandage dispenser of FIG. 4 with the right case half removed.

FIGS. 1 and 2 are perspective views of a spooled adhesive bandage dispenser 10 in accordance with a first preferred embodiment of the present invention; FIG. 3 is a perspective view of the spooled adhesive bandage dispenser 10 of FIG. 1, shown with half of the case 12 removed; and FIGS. 4 and 5 are perspective views of the right side of the spooled adhesive bandage dispenser 10 of FIG. 1, shown with the bandage roll removed in FIG. 4 and with half of the case 12 removed in FIG. 5. As shown therein, the dispenser 10 includes a case 12 in which are arranged a cartridge 70, a pair of activation wheels 52,54 and a plurality of routing features further described hereinbelow.

The case 12 itself, which may be formed of molded plastic, is comprised of two opposing case halves 18,20 connected together to define a housing that includes an exit slot 28, a thumb grip 30, a palm grip 32 and a bottom support area 38. The palm grip 32 is an area along the perimeter of the case 12, at the end of the case 12 opposite the exit slot 28, that is shaped to fit in the palm of a user's hand, and may or may not include grooves, knobs, ridges, or the like, to be held in or make contact make with a user's palm, as further described hereinbelow, thereby making it easier and/or more comfortable for the user to hold and manipulate the dispenser 10. Although the illustrated prototype is formed from an opaque material, the case 12 and one or more of the other elements are preferably manufactured from a transparent or semi-transparent material such that the current size of a bandage roll 80 in the cartridge 70 can be seen, thereby permitting a user to gauge the number of remaining adhesive bandages 84, and so that the dispenser 10 can be monitored to ensure that waste from the bandage roll 80 is properly routed to the waste core 76 as described hereinbelow. However, in at least some embodiments, including the illustrated prototype, at least the case 12 is primarily manufactured from a translucent or opaque material that may or may not include a small section of transparent material through which the number of remaining adhesive bandages 84 may be gauged. Each of these elements will be described more fully hereinbelow.

Figure 6A:
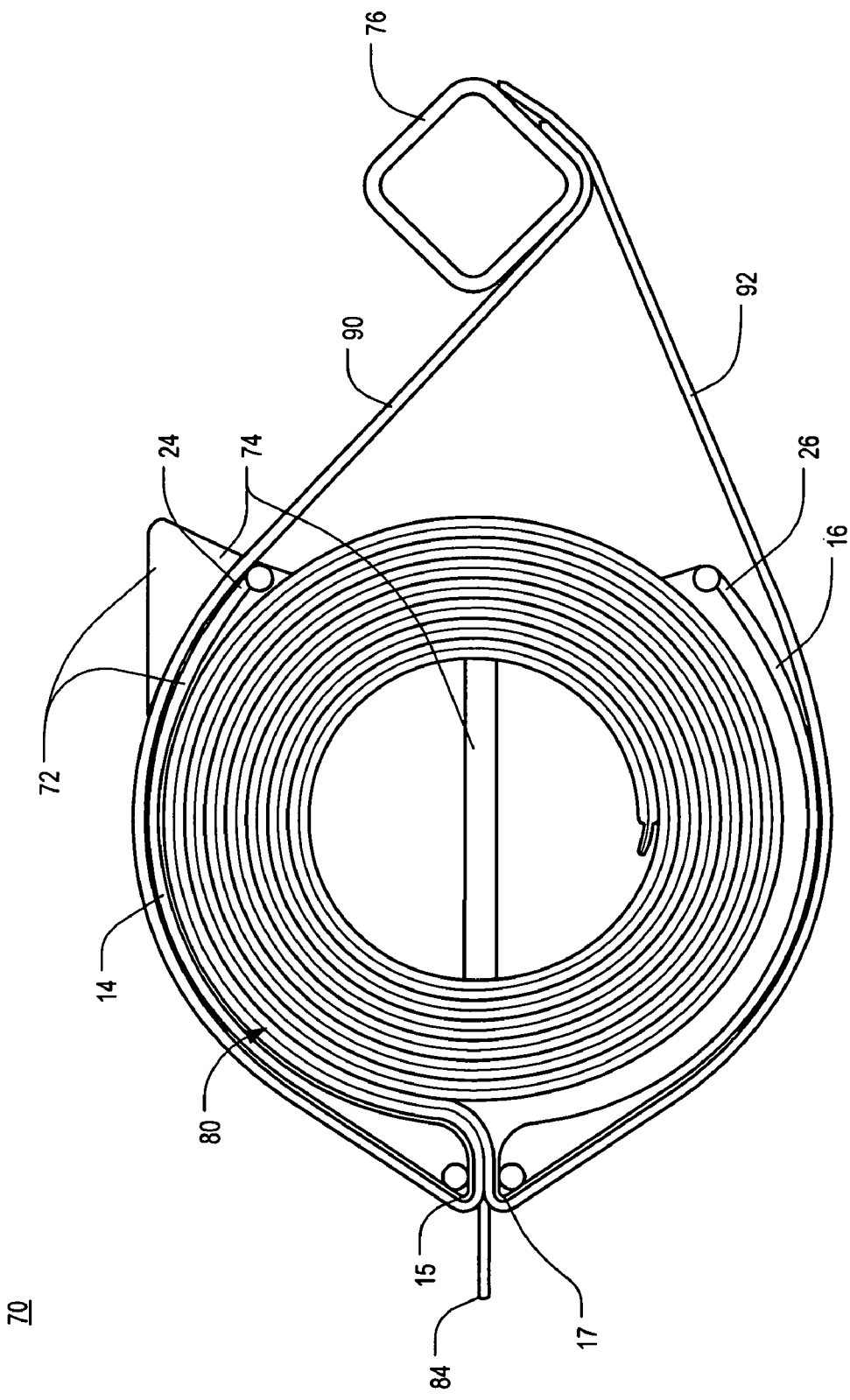
FIG. 6A is a side elevational view of the left side of the cartridge of FIG. 3.
Figure 6B:
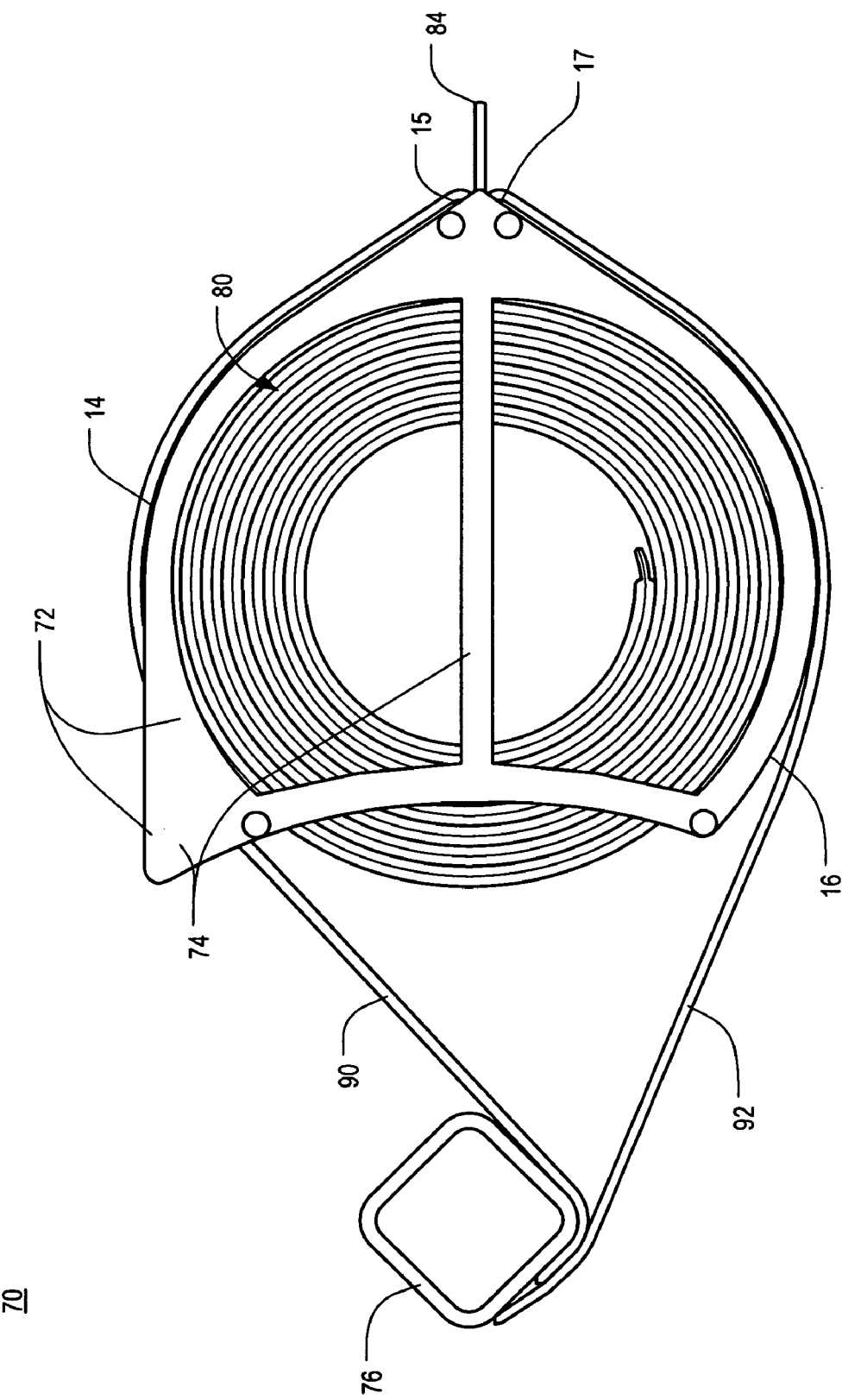
FIG. 6B is a side elevational view of the right side of the cartridge of FIG. 6A.
Figure 7:
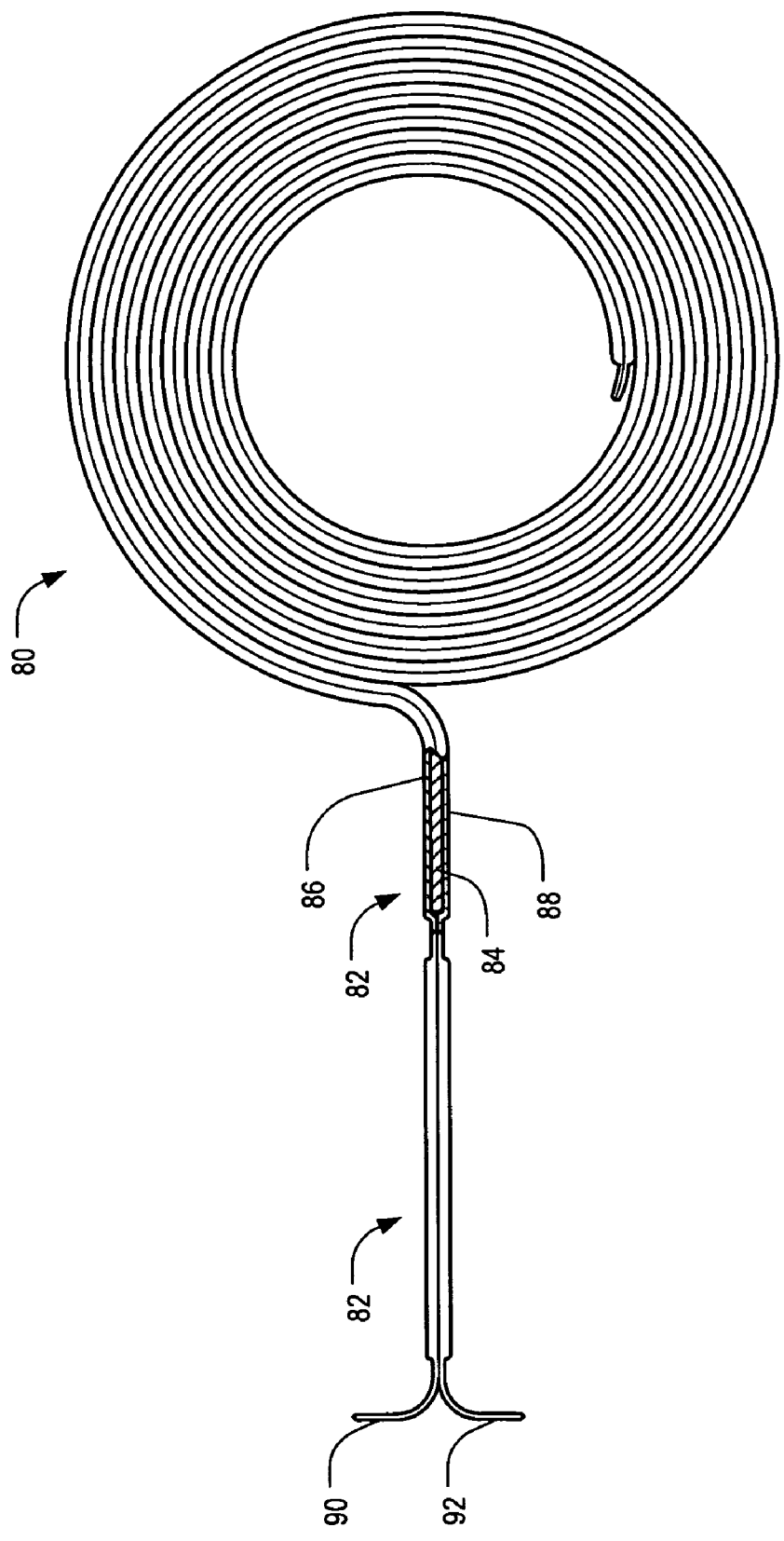
FIG. 7 is a side elevational view of the left side of the bandage roll of FIGS. 6A and 6B.

FIGS. 6A and 6B are side elevational views of the left and right sides, respectively, of the cartridge 70 of FIG. 3. The cartridge 70 includes a bandage roll 80, a frame 72 and a waste core 76. The frame 72 and the waste core 76, described further below, may each be of conventional molded plastic. FIG. 7 is a side elevational view of the bandage roll 80 of FIGS. 6A and 6B. In at least one embodiment, the bandage roll 80 comprises a relatively long strip of individual adhesive bandage packages 82, connected end-to-end as described below and illustrated in FIG. 10, that is loosely spooled with no center core to create a roll. In at least one other embodiment, the bandage roll 80 comprises a similar strip of individual adhesive bandage packages 82 that is spooled around a central core to create a roll.

As perhaps best shown in FIG. 7, each bandage package 82 includes an individual adhesive bandage 84 sandwiched between two layers of packaging 86,88 such that the bandage 84 is encased in a sealed envelope. It will be appreciated that bandages of any type or construction may be dispensed according to one or more preferred embodiments of the present invention, including plastic, fabric, clear, waterproof, and the like. Each packaging layer 86,88 is a continuous strip of material that is sealed to the other layer, such as by heat sealing, around the perimeter of each bandage 84 and at the ends of each bandage 84. The properties of the material are such that the bandage envelopes thus created are able to maintain the bandages 84 in a sterile environment until opened for use as described below. One material suitable for use in one or more preferred embodiments of the present invention is a conventional paper wrapper, but it will be appreciated that other materials capable of keeping the bandages 84 sterile may likewise be used.

The dimensions of the case 12 as well as many of the other elements of the dispenser 10 may depend upon the dimensions of the bandages 84 being dispensed therefrom. It will be appreciated that the dimensions of the dispenser 10 may be varied to accommodate the various sizes of bandages that are or may be available, such as finger size, junior size, knee size, elbow size, and the like.

The packaging layers 86,88 are further capable of being unsealed, thereby exposing the bandages 84 contained therebetween one-by-one, without being torn or broken, thereby permitting the unsealed layers 86,88 to be collected as waste strips 90,92 on the waste core 76, as shown in FIGS. 7A and 7B. A leading end of each waste strip 90,92 is wrapped around or otherwise connected to the waste core 76 such that rotation of the waste core 76 causes the waste strips 90,92 to be wound therearound. Notably, each waste strip 90,92 is wound around the waste core 76 in the same direction, such that rotation in the proper direction causes both waste strips 90,92 to be wound simultaneously. In at least some embodiments, the portion of each waste strip 90,92 near its leading end defines a leader, and may be formed from the same material used for the remainder of the packaging layers 86,88 or from a different material.

The waste core 76 is a structure defining an exterior winding surface and means for coupling the core 76 to the activation wheels 52,54 as described below. Together, the waste core 76 and activation wheels 52,54 may, in at least some embodiments, define a take-up reel assembly. Further, in at least some embodiments, the exterior winding surface is non-circular, or more particularly, is oblong or includes flat surfaces in addition to curved surfaces. In addition to providing some advantage in the winding operation, such a non-circular shape may more conveniently be used on the interior of the core 76 as well; such a shape makes it easier to couple the core 76 to a correspondingly-shaped structure on the activation wheels 52,54, further described hereinbelow, because the non-circular shape prevents rotation, i.e., free-wheeling, of the core 76 without corresponding rotation of the activation wheels 52,54.

The cartridge frame 72 includes a generally planar base 74 and a pair of waste guides 14,16 extending perpendicularly therefrom. The base 74 is adapted to support and position the waste guides 14,16 within the case 12. When the dispenser 10 is placed in an upright position, as shown in FIG. 1, the cartridge frame base 74 is oriented vertically along one side of the dispenser 10. Coupling features, adapted to mate with corresponding features on the interior of one or both of the case halves 18,20, may be provided in appropriate locations on the base 74 and, in at least some embodiments, on the waste guides 14,16. The waste guides 14,16 are shaped, spaced and dimensioned to accommodate the full diameter of the bandage roll 80 therebetween. Proximal ends 15,17 of the waste guides 14,16 are provided with generally uniform curvature and manufactured with relatively frictionless surfaces such that the packaging layers 86,88 may be guided smoothly therearound as can be seen, for example, in FIG. 6A, and as further described hereinbelow. In at least some embodiments, the frame 72 together with the bandage roll 80 carried therein may define a dispensing reel assembly.

Figure 8:
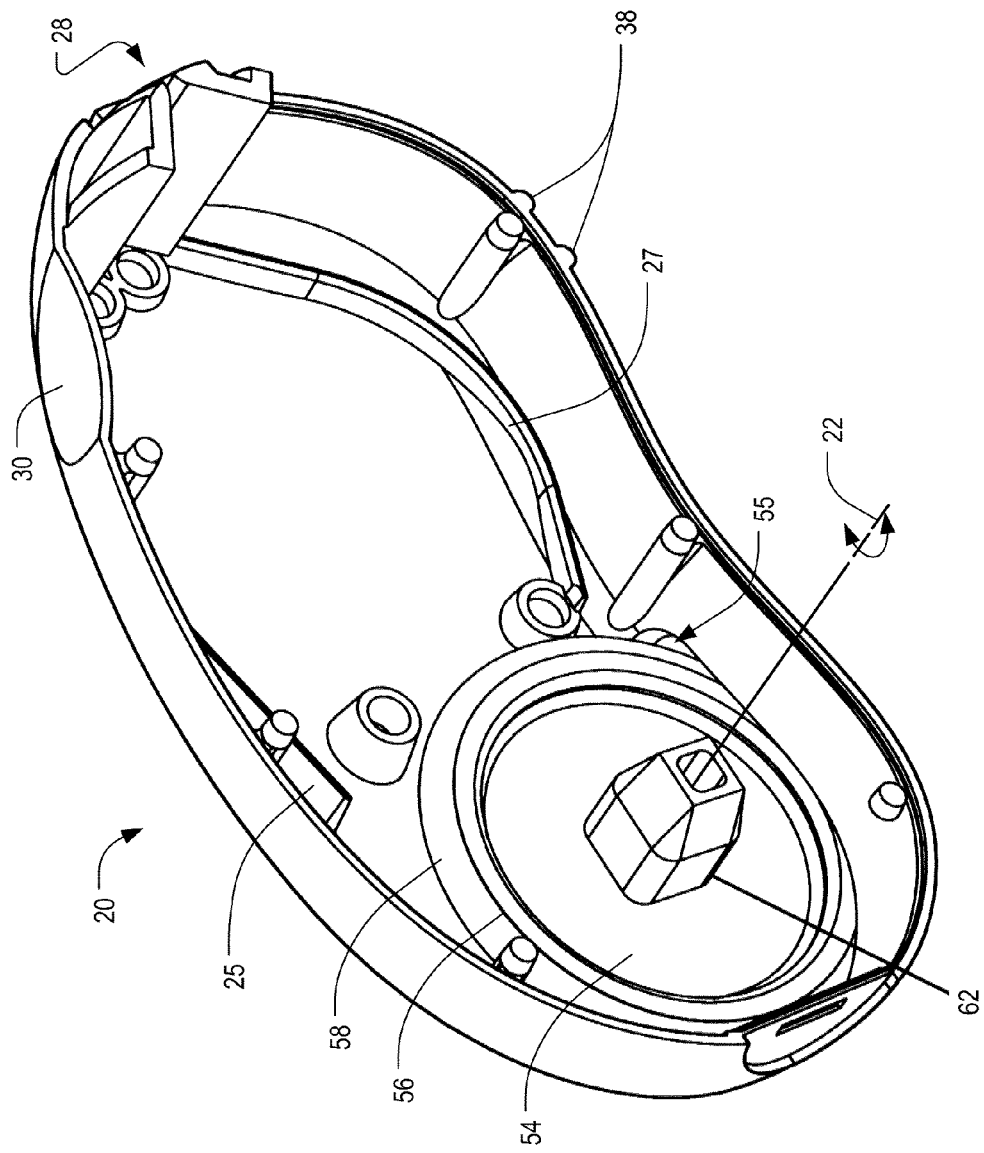
FIG. 8 is a perspective view of the left case half of the spooled adhesive bandage dispenser of FIG. 1.

FIG. 8 is a perspective view of the left case half 20 of the spooled adhesive bandage dispenser 10 of FIG. 1. The activation wheels 52,54, which are parallel to each other but spaced apart, are each rotatably attached to a respective case half 18,20 such that their rotation relative to the case 12 occurs about a common axis of rotation 22. A further coupling, such as in the form of an extension 60,62 having a distal end whose forms a male coupling for engagement with a female coupling formed by the interior of the waste core 76. In such an arrangement, each extension may, in at least some embodiments, have a cross-sectional shape that matches that of the interior of the waste core 76, and in particular that matches the oblong or other non-circularly-shaped interior of the waste core 76, described above. As noted previously, the non-circular shape of the male and female couplings prevents rotation, i.e., free-wheeling, of the core 76 without corresponding rotation of the activation wheels 52,54.

It will be appreciated that, in at least some embodiments, the design and construction of the waste core may be varied without departing from the scope of the present invention. For example, the waste core may be constructed from a biodegradable material, such as cardboard, rather than molded plastic. The waste core may be cylindrical and provided with a central bore through which an axle or the like may be inserted fully therethrough, rather than interlocking with the extensions 60,62 on the activation wheels 52,54 as described and illustrated herein. Two separate waste cores may likewise be utilized, one for each waste strip 90,92.

Though generally disposed in the interior of the case 12, each activation wheel 52,54 is partially exposed to the exterior via a respective opening 53,55 in the bottom of the case 12. Any of a variety of features may be applied to the perimeter or rim 56 of each activation wheel 52,54 to permit a user to easily rotate the activation wheels 52,54 by manipulating one or both of the rims 56 thereof. In the illustrated embodiment, a rubber or plastic band 58 is wrapped around the rim 56 to provide this function, but in some embodiments, grooves, knobs, ridges, or the like, some of which are further described and illustrated herein, may be formed or otherwise provided along the rim 56, or the rim 56 may be provided with a textured surface or formed or otherwise manufactured from a material providing an increased level of friction.

As perhaps best illustrated in FIGS. 4 and 5, distal ends 24,26 of the waste guides 14,16 extend toward the two activation wheels 52,54, terminating just outside the perimeters or rims 56 thereof. The width of each waste guide 14,16 and the size of the gap between the activation wheels 52,54 each correspond to the width of the waste 90,92, as will be further described hereinbelow. The interior of one or both of the case halves 18,20 may further include supplemental waste guides 25,27 that correspond to, and align with, the waste guides 14,16 of the cartridge 70. In some embodiments, the supplemental waste guides 25,27 may provide a lateral extension to the cartridge waste guides 14,16. In other embodiments, the supplemental waste guides 25,27 are offset from the outer surfaces of the waste guides 14,16, such as is shown in FIG. 4, thereby more narrowly defining the path along which waste strips 90,92 are guided as described below.

Figure 9:
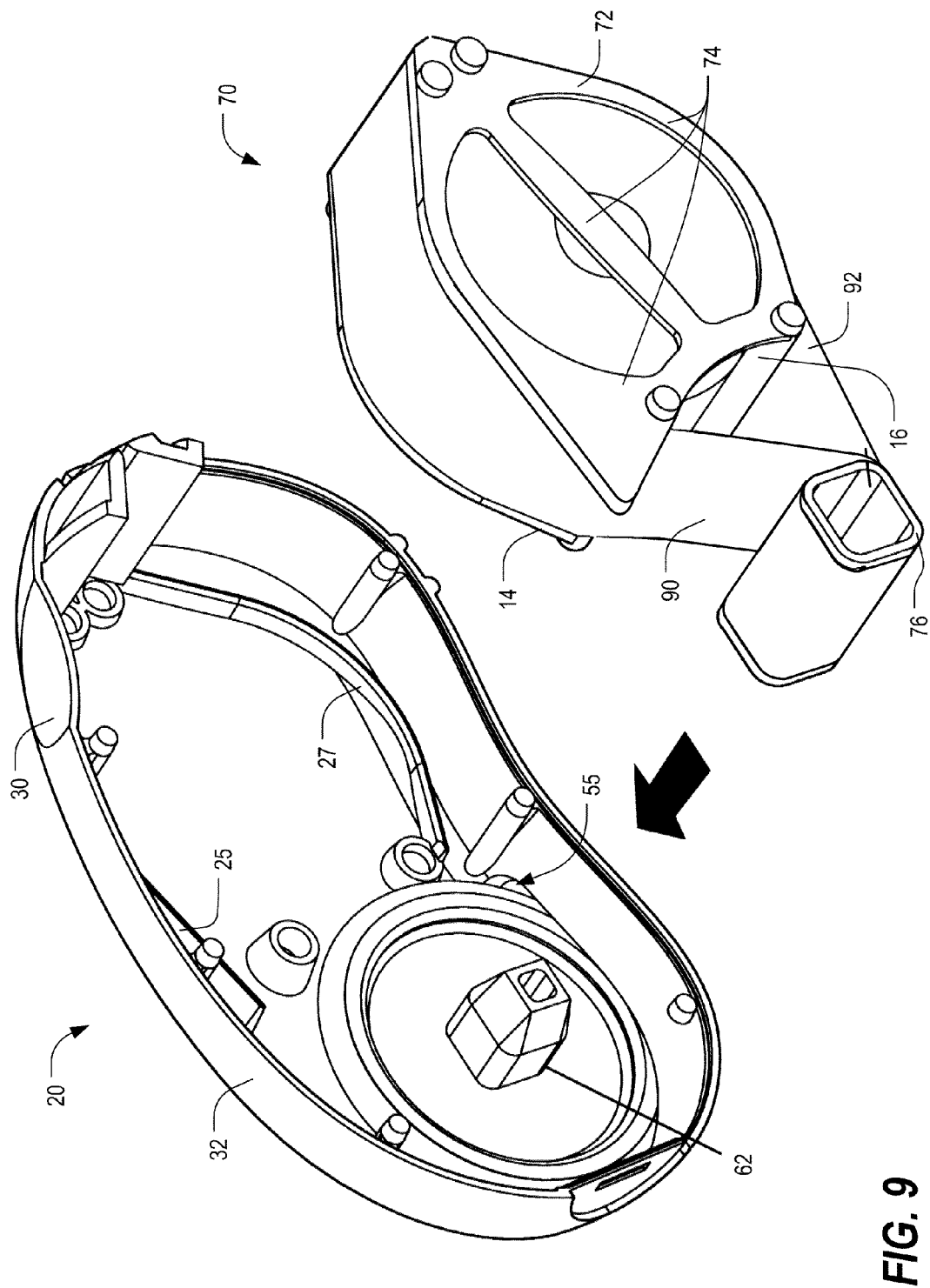
FIG. 9 is a perspective view of the cartridge of FIGS. 6A and 6B being loaded into the left case half of FIG. 8.
Figure 10:
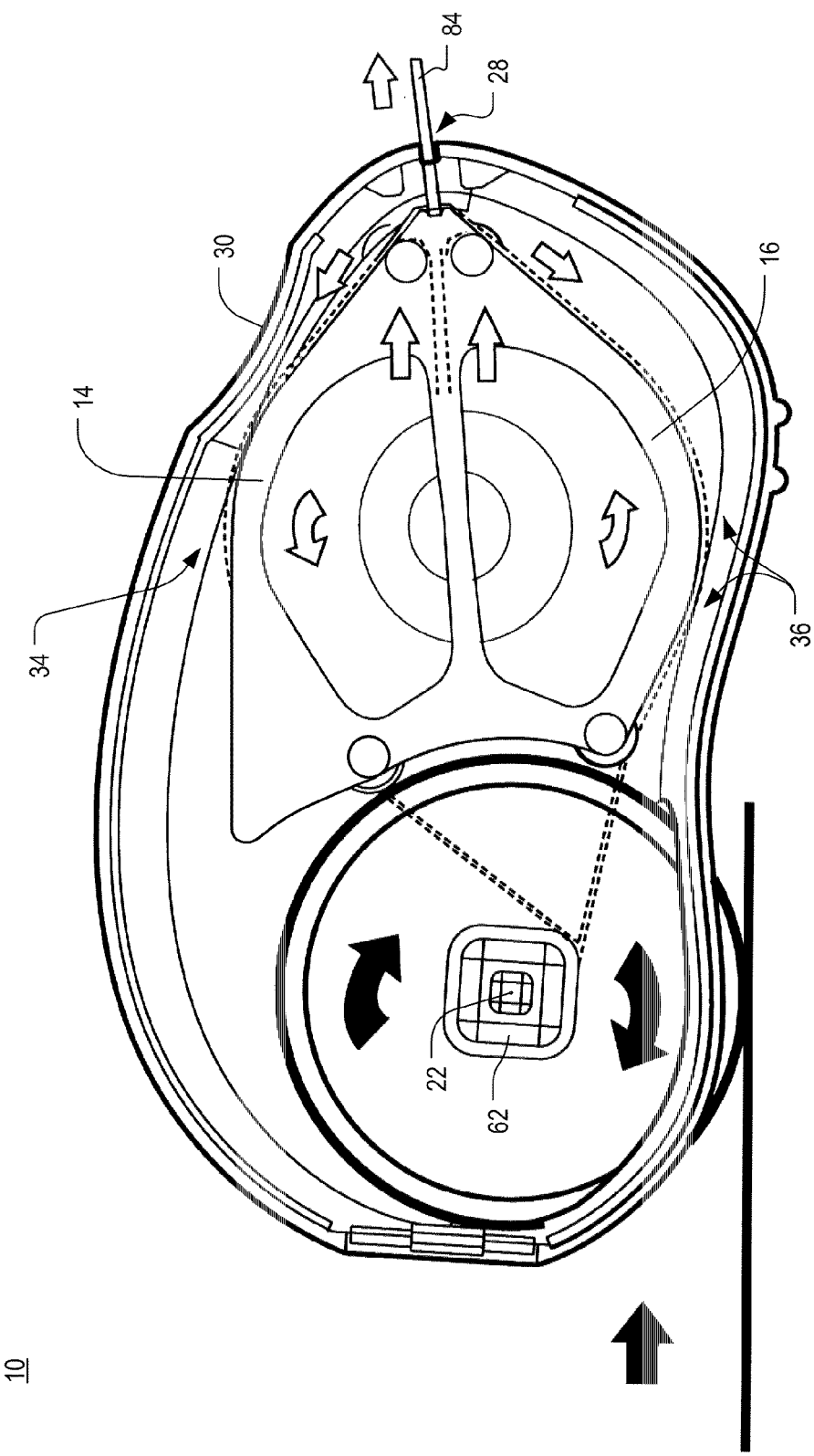
FIG. 10 is a partially schematic side elevational view of the cartridge installed in the left case half, illustrating a first step in the operation of the dispenser.
Figure 11:
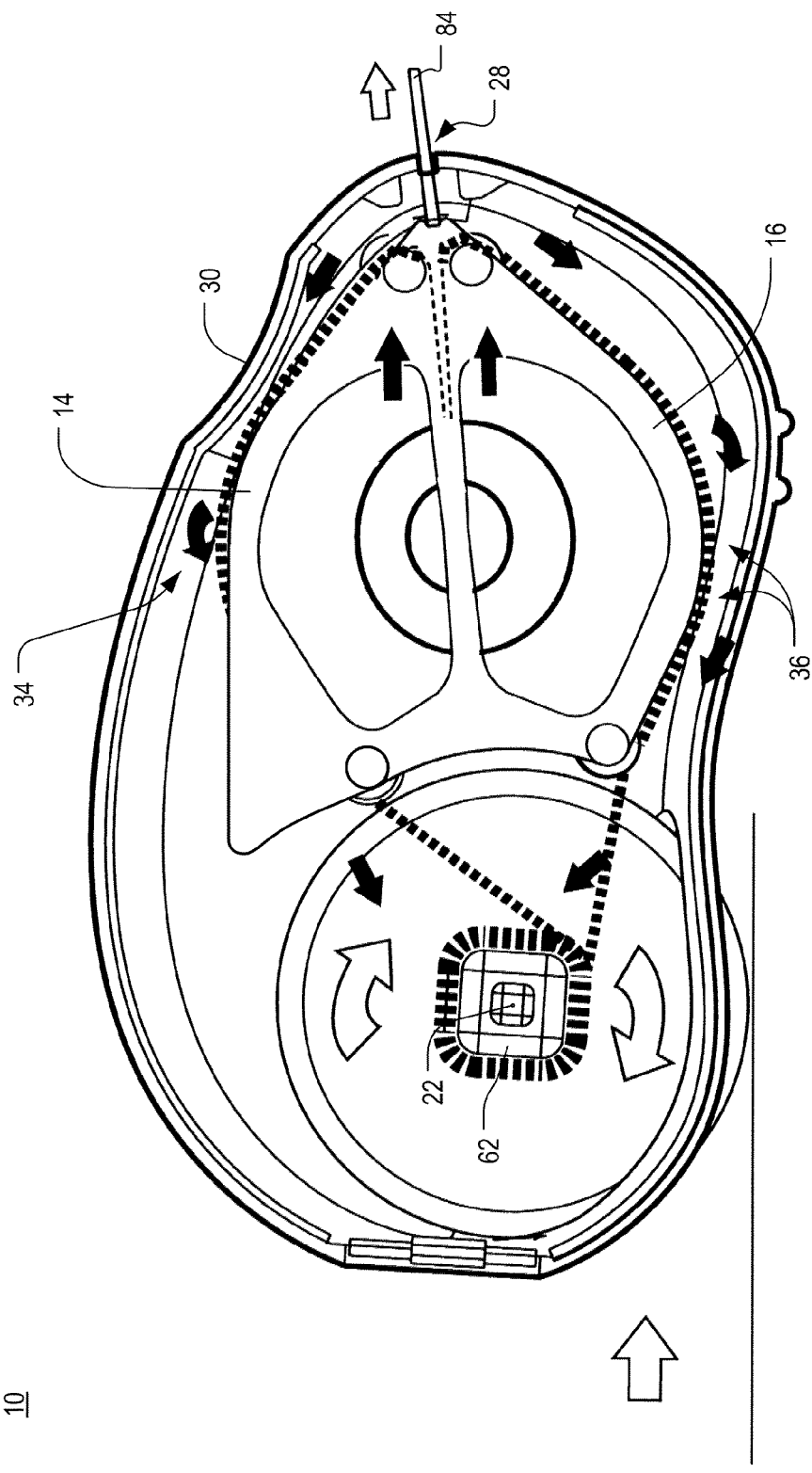
FIG. 11 is a partially schematic side elevational view of the cartridge installed in the left case half, illustrating a second step in the operation of the dispenser.
Figure 12:
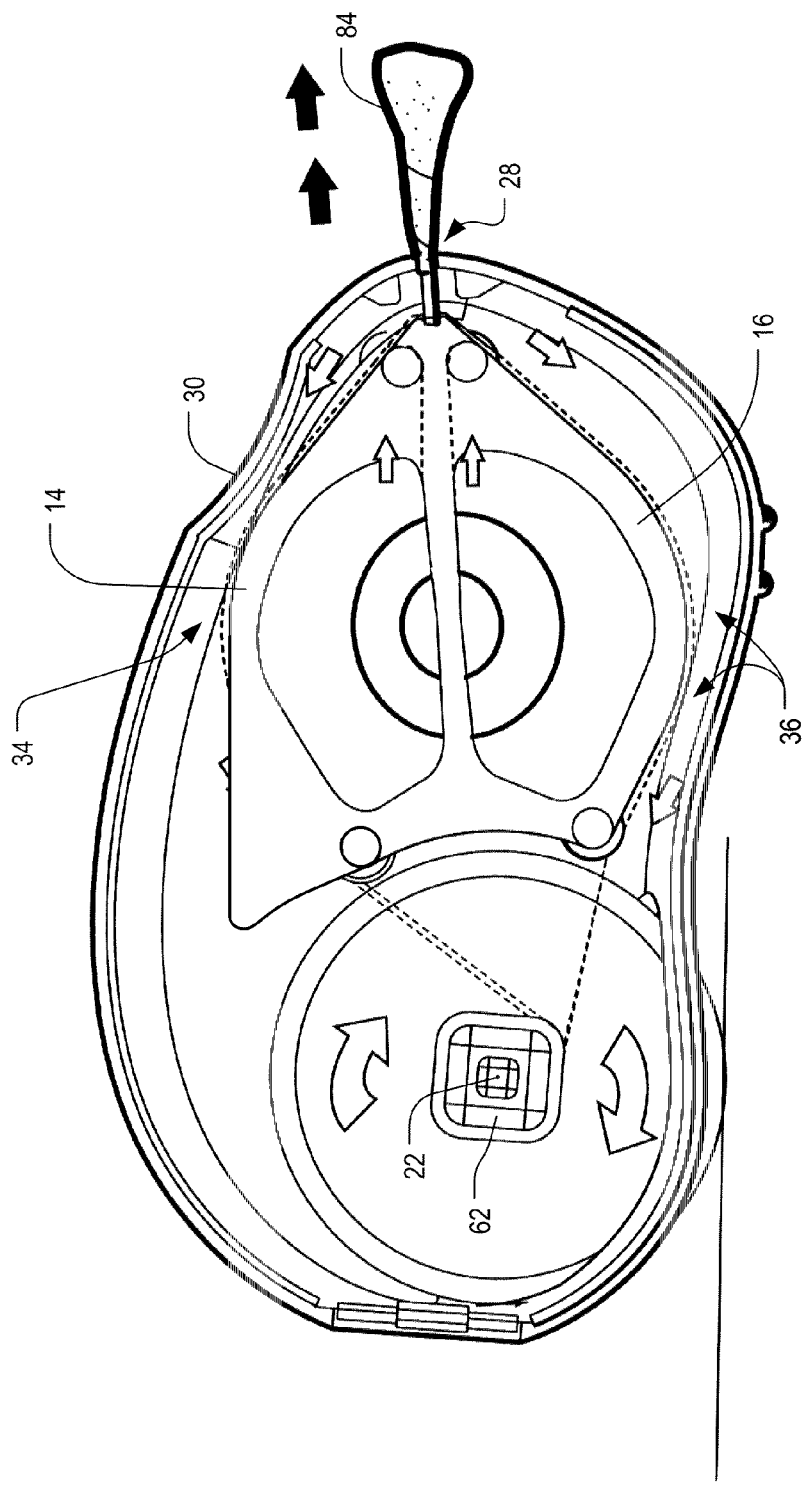
FIG. 12 is a partially schematic side elevational view of the cartridge installed in the left case half, illustrating a third step in the operation of the dispenser.

FIG. 9 is a perspective view of the cartridge of FIGS. 6A and 6B being loaded into the left case half 20 of FIG. 8, and FIGS. 10-12 are partially schematic side elevational views of the cartridge installed in the left case half, illustrating various steps in the operation of the dispenser 10. The cartridge 70 is installed in the case 12 such that the frame 72 is mounted in its intended position in the case 12 and the waste core 76 is coupled to the extensions 60,62 on the interior sides of the activation wheels 52,54. When properly arranged in the case 12, the waste guides 14,16 establish two waste channels 34,36. More particularly, when the dispenser 10 is placed in an upright position, as shown in FIG. 10, a first waste channel 34 is established between a first waste guide 14 and the interior of the top of the case 12, and a second waste channel 36 is established between a second waste guide 16 and the interior of the bottom of the case 12. Their function may be understood as follows. When the cartridge 70 is installed in the case 12, the leaders of the waste strips 90,92 are routed from where the waste strips 90,92 initially separate from each other, around the proximal ends 15,17 of the waste guides 14,16, through the waste channels 34,36 defined between the waste guides 14,16 and the interior walls of the case 12, and past the distal ends 24,26 of the waste guides 14,16 to the waste core 76. With the cartridge 70 in place, the case 12 may be closed, thereby placing the dispenser 10 in a ready-to-use state.

In operation, a user may grasp the dispenser 10, making use of the palm grip 32 and thumb grip 30 as desired, and at the same time cause the activation wheels 52,54 to be turned. Such action, if applied to the activation wheels 52,54 in the proper rotational direction, causes the waste strips 90,92, starting with their leaders, to be wound around the waste core 76. As the waste strips 90,92 are wound, the unseparated strip of bandage packages 82 is correspondingly unwound from the bandage roll 80. The tension placed on the packaging layers 86,88 as the waste strips 90,92 are pulled in generally opposite directions at the proximal ends 15,17 of the waste guides 14,16 causes the packaging layers 86,88 to unseal from each other and separate. As the rotational motion of the activation wheels 52,54 and waste core 76 continues, and greater lengths of the packaging layers 86,88 are separated and routed toward the waste core 76 as waste strips 90,92, the first or next adhesive bandage 84 in the strip of bandage packages 82 is gradually exposed. A leading end of this bandage 84 slides naturally between the proximal ends 15,17 of the waste guides 14,16 and straight through the exit slot 28, where it may be retrieved by the user. The bandage 84 thus stays safely enclosed within the individual envelope of its respective bandage package 82 until forced out by the user.

In the illustrated embodiment, the cartridge 70 is of a replaceable type, wherein the entire cartridge 70, including the frame 72, the waste core 76 and all of the waste strips 90,92 wrapped therearound, may be removed and replaced by a new cartridge 70. In other embodiments, the frame remains but the waste core 76, including the waste strips 90,92, is removed and a new bandage roll 80 and waste core 76 are installed. In at least one commercial application of either such embodiment, the dispenser 10 is made available to consumers in a state in which it is preloaded with a full roll 80, while in at least one other such commercial application each dispenser 10 comes unloaded but ready for loading by the user. In either such commercial application, replacement cartridges 70 or rolls 80 may be sold or otherwise offered together with each dispenser 10, or such replacement cartridges 12 or rolls 80 may be sold or otherwise offered separately. In at least some other embodiments, neither the cartridge 70 nor the bandage roll 80 is individually replaceable, and the entire dispenser 10 must be replaced once the roll 80 is spent.

With particular reference to FIGS. 3, 5 and 9, two other features that may be present in at least some embodiments of the present invention are further noted. In particular, the dispenser 10 may include additional features on the interior of the case 12 to facilitate assembly, a better fit between the case halves 18,20, or to better guide bandages 84 and waste strips 90,92 within the case 10. For example, a nosepiece 33 may be provided at the front of the case 12, adjacent the exit slot 28. Such a nosepiece 33 includes a pair of planar flanges that are disposed in close proximity to the proximal ends 15,17 of the waste guides 14,16 such that the waste strips 90,92 are routed more smoothly, with fewer entanglements or the like, around the waste guide ends 15,17. An additional gap created between proximate edges of the two planar flanges may help in more smoothly guiding each unwrapped bandage 84 through the exit slot 28. In another feature, a series of assembly tabs 35 may be provided around the periphery of one or both of the case halves 18,20. These tabs 35 help create a friction fit between the two halves 18,20 of the case 12. Some of the tabs 35 may also effectively create narrower waste channels 34,36, potentially further helping to avoid entanglements and the like within the waste channels 34,36. In another feature, one or more latches 31 may be provided to facilitate opening the case 12, such as by separating the two case halves 18,20, thereby facilitating the replacement of the cartridge 70 or maintenance of or service to the internal components, such as fixing a jammed waste strip 90,92 or bandage 84.

Figure 13:
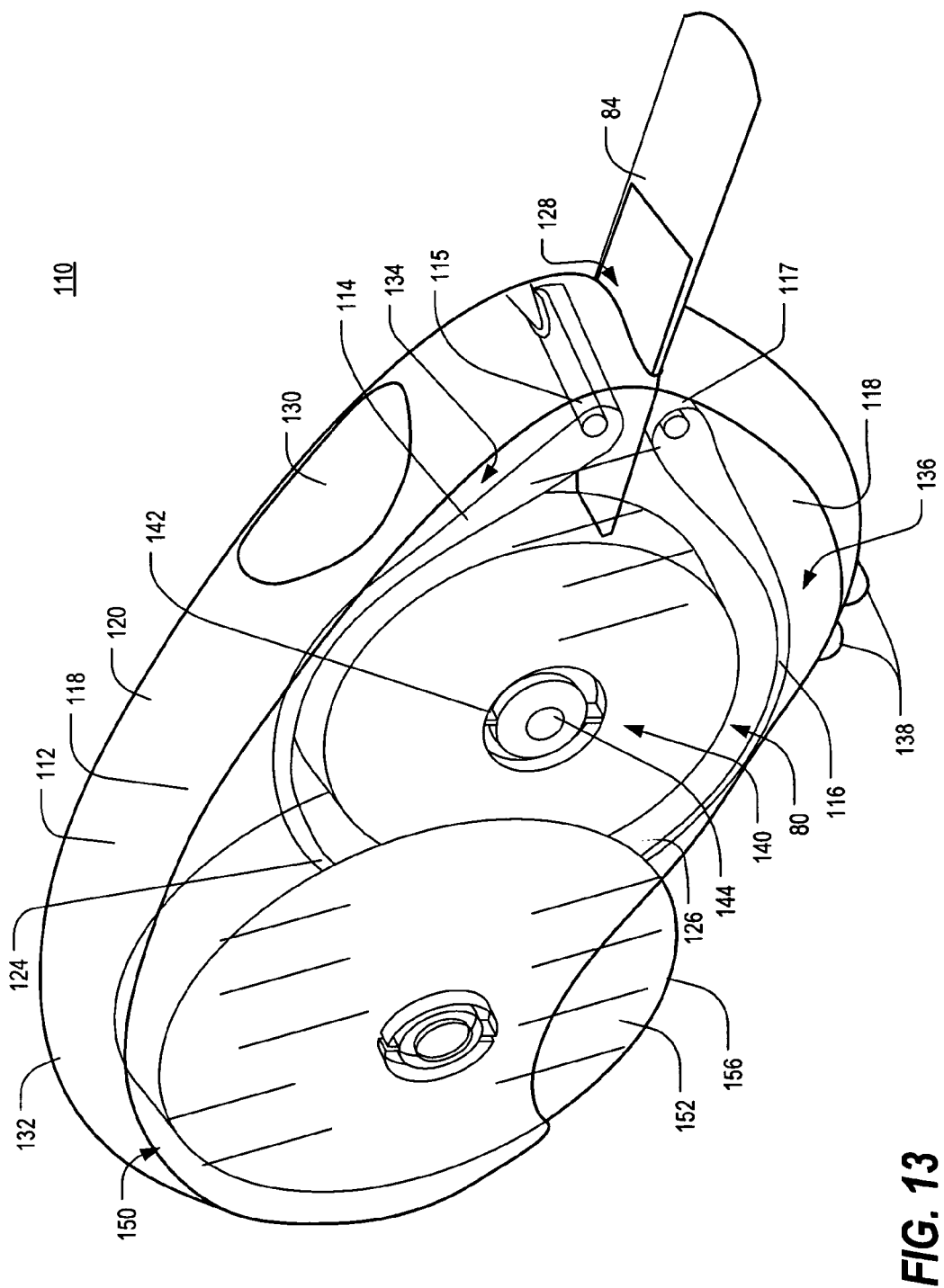
FIG. 13 is a perspective view of the right side of a spooled adhesive bandage dispenser in accordance with a second preferred embodiment of the present invention.

FIG. 13 is a perspective view of the right side of a spooled adhesive bandage dispenser 110 in accordance with a second preferred embodiment of the present invention. As shown therein, the dispenser 110 includes a case 112 in which are arranged a dispensing reel assembly 140, a take-up reel assembly 150, and a pair of waste guides 114,116. The case 112 itself is comprised of two opposing case halves 118,120 connected together to define a housing that includes an exit slot 128, a thumb grip 130, a palm grip 132 and a bottom support area 138. The palm grip 132 is an area along the perimeter of the case 112, at the end of the case 112 opposite the exit slot 128, that is shaped to fit in the palm of a user's hand, and may or may not include grooves, knobs, ridges, or the like, to be held in or make contact make with a user's palm, as further described hereinbelow, thereby making it easier and/or more comfortable for the user to hold and manipulate the dispenser 110. The case 112 and one or more of the other elements are preferably manufactured from a transparent or semi-transparent material such that the current size of a bandage roll 80 (not shown in FIG. 14 but visible in FIG. 13) carried on the dispensing reel assembly 140 can be seen, thereby permitting a user to gauge the number of remaining adhesive bandages 84, and so that the dispenser 110 can be monitored to ensure that waste from the bandage roll 80 is properly routed to the take-up reel assembly 150. However, in at least some embodiments, at least the case 112 is primarily manufactured from a translucent or opaque material that may or may not include a small section of transparent material through which the number of remaining adhesive bandages 84 may be gauged. Each of these elements will be described more fully hereinbelow.

Figure 14:
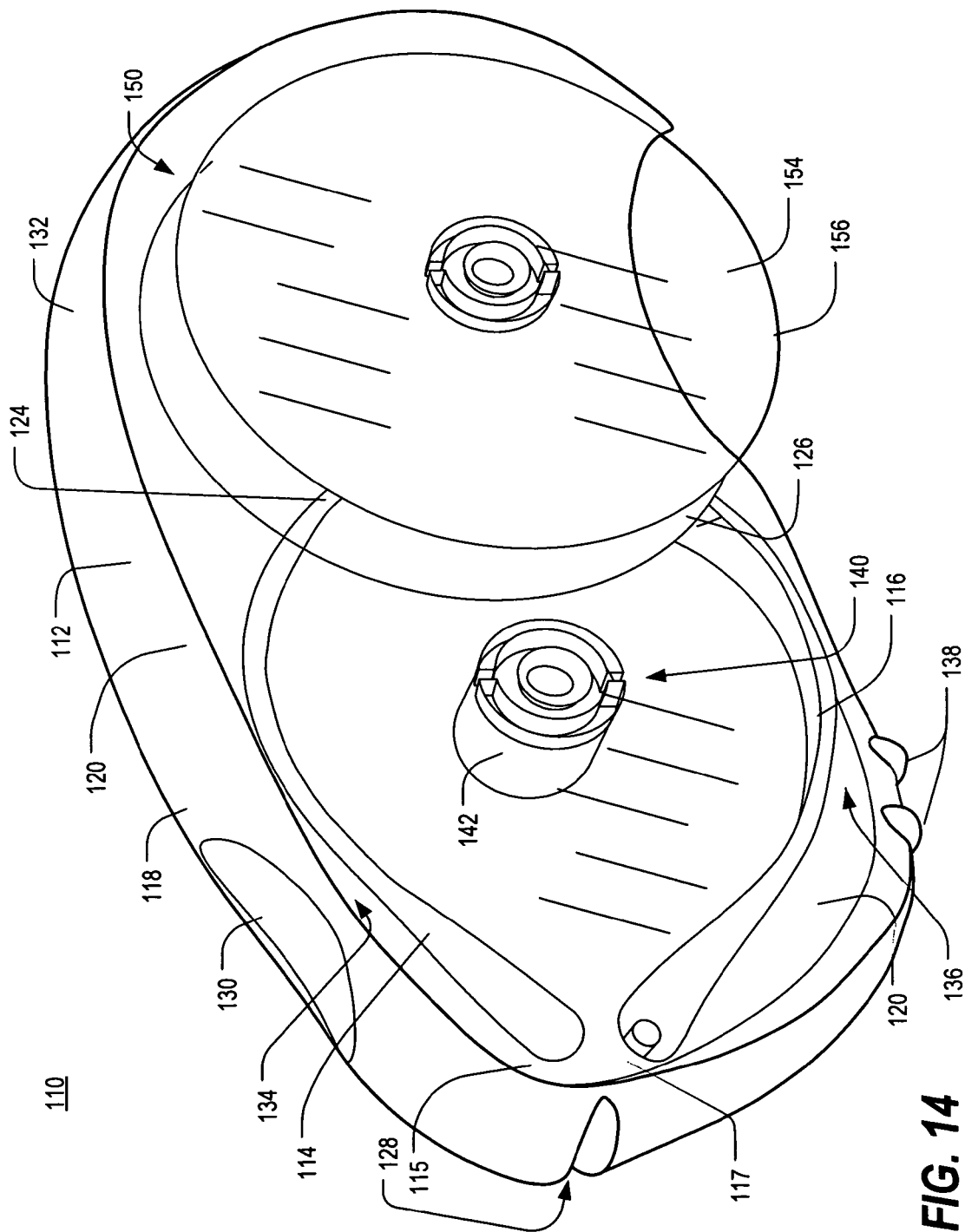
FIG. 14 is a perspective view of the left side of the spooled adhesive bandage dispenser of FIG. 13, shown with the bandage roll removed.

FIG. 14 is a perspective view of the left side of the spooled adhesive bandage dispenser 110 of FIG. 13. The dispensing reel assembly 140 includes a first axle 144, extending between the two case halves 118,120, that carries a dispensing reel 142. In this embodiment, the waste guides 114,116 are preferably molded into the case 112, but are shaped, spaced and dimensioned such that the dispensing reel assembly 140, and a bandage roll 80 carried thereon, may be accommodated therebetween. The bandage roll 80 is of generally similar construction to that of FIG. 7. Proximal ends 115,117 of the waste guides 114,116 are provided with generally uniform curvature and manufactured with relatively frictionless surfaces such that waste material may be guided smoothly therearound in similar manner to that described and illustrated in FIGS. 1-12. The waste guides 114,116 are further arranged such that a respective waste channel 134,136 is established between each guide 114,116 and the top or bottom of the case 112, respectively. The waste channels 134,136 and their function will be further described hereinbelow.

As is partially visible in FIG. 13, the take-up reel assembly 150 includes two parallel but spaced apart activation wheels 152,154 carried by a second axle (not shown) that also extends between the two case halves 118,120. Though generally disposed in the interior of the case 112, the activation wheels 152,154 are partially exposed to the exterior via a respective opening in the bottom of the case 112. Grooves, knobs, ridges, or the like may be formed or otherwise provided along the perimeter or rim 156 of each activation wheel 152,154, or the rim 156 may be provided with a textured surface or formed or otherwise manufactured from a material providing an increased level of friction, thereby permitting a user to easily rotate the activation wheels 152,154 by manipulating one or both of the rims 156 thereof. Distal ends 124,126 of the waste guides 114,116 extend into the space or gap between the two activation wheels 152,154, terminating just inside the perimeters thereof. The width of each waste guide 114,116 and the size of the gap between the activation wheels 152,154 each correspond to the width of the waste 90,92, as will be further described hereinbelow.

The bandage roll 80 is installed in the case 112 by opening the case 112 and mounting the bandage roll 80 on or in the dispensing reel assembly 140. With the bandage roll 80 in place, the leaders of the waste strips 90,92 are routed from where the waste strips 90,92 initially separate from each other, around the proximal ends 115,117 of the waste guides 114,116, through the waste channels 134,136 defined between the waste guides 114,116 and the interior walls of the case 112, and past the distal ends 124,126 of the waste guides 114,116 to the take-up reel assembly 150. With the bandage roll 80 thus installed, the case 112 may be closed, thereby placing the dispenser 110 in a ready-to-use state.

In operation, a user may grasp the dispenser 110, making use of the palm grip 132 and thumb grip 130 as desired, and at the same time cause the activation wheels 152,154 to be turned. Such action, if applied to the activation wheels 152, 154 in the proper rotational direction, causes the waste strips 90,92, starting with their leaders, to be wound around the take-up reel assembly 150. As the waste strips 90,92 are wound, the unseparated strip of bandage packages 82 is correspondingly unwound from the bandage roll 80. The tension placed on the packaging layers 86,88 as the waste strips 90,92 are pulled in generally opposite directions at the proximal ends 115,117 of the waste guides 114,116 causes the packaging layers 86,88 to unseal from each other and separate. As the rotational motion of the take-up reel assembly 150 continues, and greater lengths of the packaging layers 86,88 are separated and routed toward the take-up reel assembly 150 as waste strips 90,92, the first or next adhesive bandage 84 in the strip of bandage packages 82 is gradually exposed. A leading end of this bandage 84 slides naturally between the proximal ends 115,117 of the waste guides 114,116 and straight through the exit slot 128, where it may be retrieved by the user. The bandage 84 thus stays safely enclosed within the individual envelope of its respective bandage package 82 until forced out by the user.

In at least some embodiments, the bandage roll 80 is of a replaceable type, wherein a spent roll 80 may be removed from the dispensing reel assembly 140 and replaced by a new roll 80. In at least one commercial application of such an embodiment, the dispenser 110 is made available to consumers in a state in which the dispensing reel assembly 140 comes preloaded with a full roll 80, while in at least one other such commercial application the dispensing reel assembly 140 comes unloaded but ready for loading by the user. In either such commercial application, dispensers 110 may be sold or otherwise offered to consumers with full or replacement rolls 80 offered together therewith or offered separately. In at least some other embodiments, the bandage roll 80 is not individually replaceable, and the entire dispenser 110 must be replaced once the roll 80 is spent.

Figure 15:
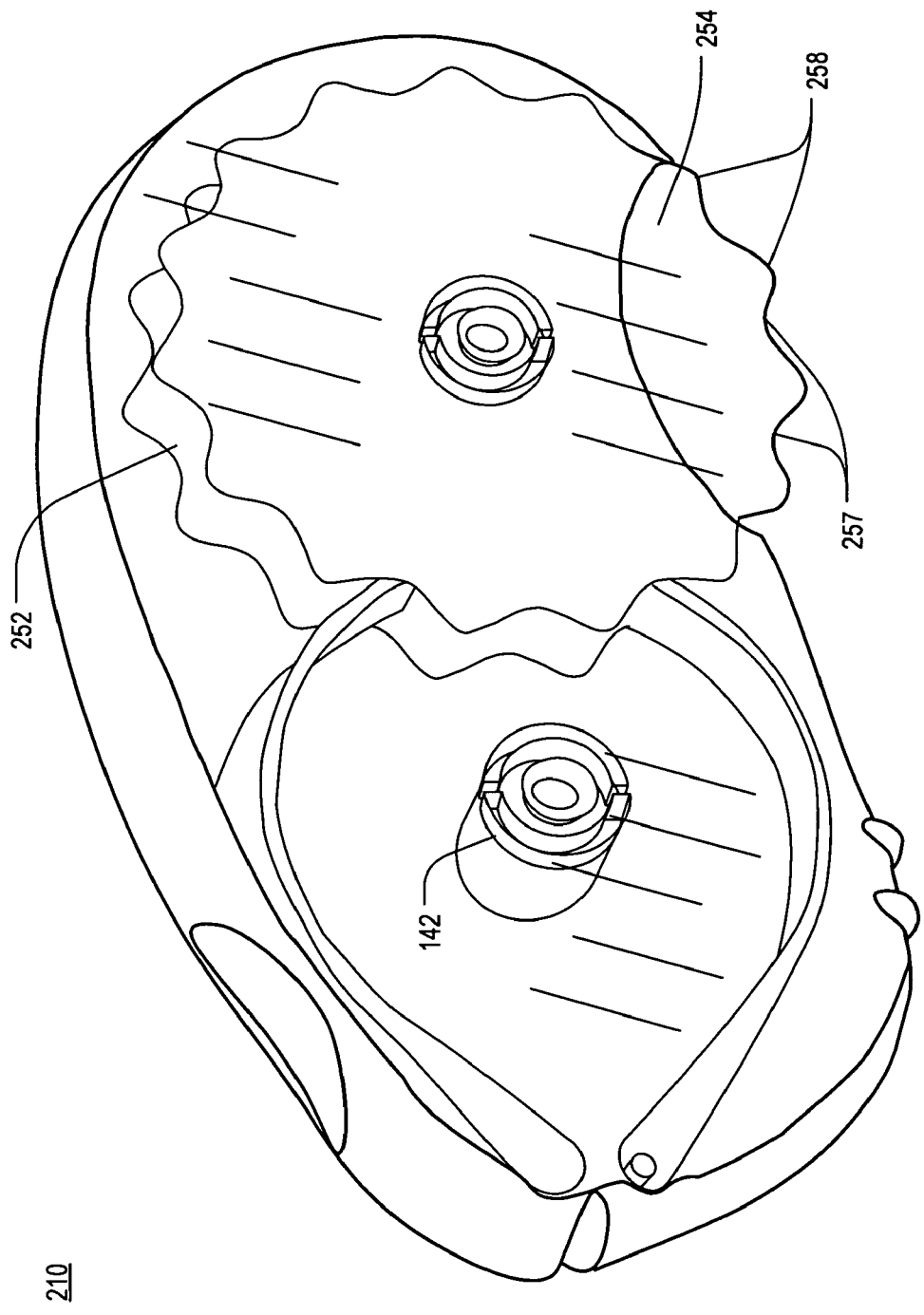
FIG. 15 is a perspective view of the left side of a spooled adhesive bandage dispenser in accordance with a third preferred embodiment of the present invention.

FIG. 15 is a perspective view of the left side of a spooled adhesive bandage dispenser 210 in accordance with a third preferred embodiment of the present invention. The dispenser 210 may function as in any one of the preceding embodiments; however, in addition the outer perimeter or rim 256 of each activation wheel 252,254 may be constructed to have spaced grooves 257 with a raised point or knob 258 in between each pair of adjacent grooves 257. In at least one embodiment these grooves 257 are all of uniform shape, length and depth, and each point 258 is spaced evenly apart from the next point 258. In at least one other embodiment, however, these grooves 257 are not of uniform length or depth and each point 258 may not be spaced evenly apart from the next point 258.

FIGS. 16-19 are perspective views of a spooled adhesive bandage dispenser 310 in accordance with a fourth preferred embodiment of the present invention. The dispenser 310 may be generally similar to any one of the preceding embodiments; however, one or more additional alteration is included in this fourth preferred embodiment. More particularly, the palm grip 332, which is an area along the perimeter of the case 312, at the end of the case 312 opposite the exit slot 328, that is shaped to fit in the palm of a user's hand, may include a multitude of indentations 333 running along its length. In at least one embodiment the indentations 333 are roughly elliptical in nature, oriented perpendicular to the length of the case 312, and uniform in size and depth. However, in at least one other embodiment, the indentations 333 may be non-uniform in size, shape, or depth.

Figure 16:
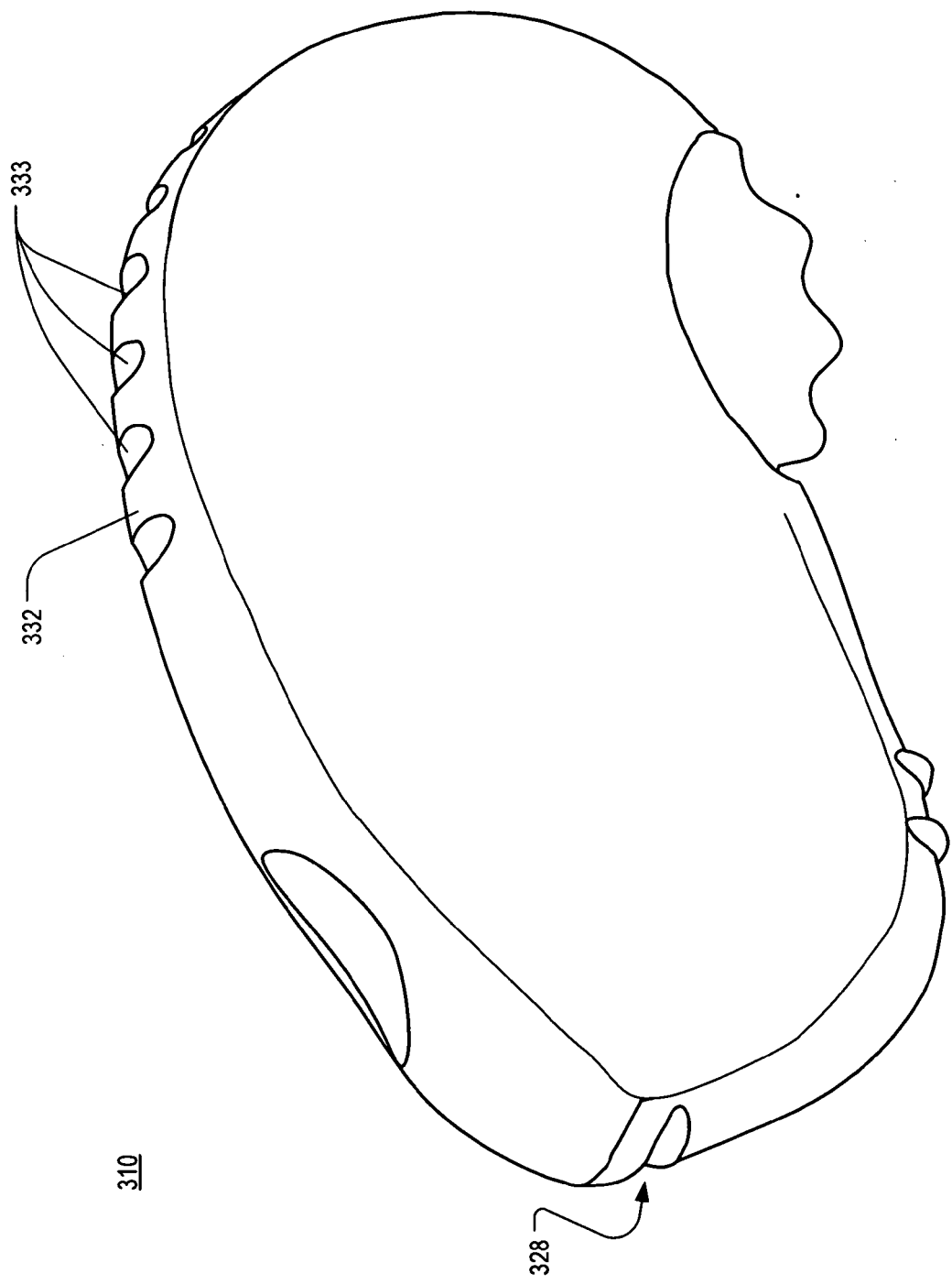
FIG. 16 is a perspective view of the left side of a spooled adhesive bandage dispenser in accordance with a fourth preferred embodiment of the present invention.
Figure 17:
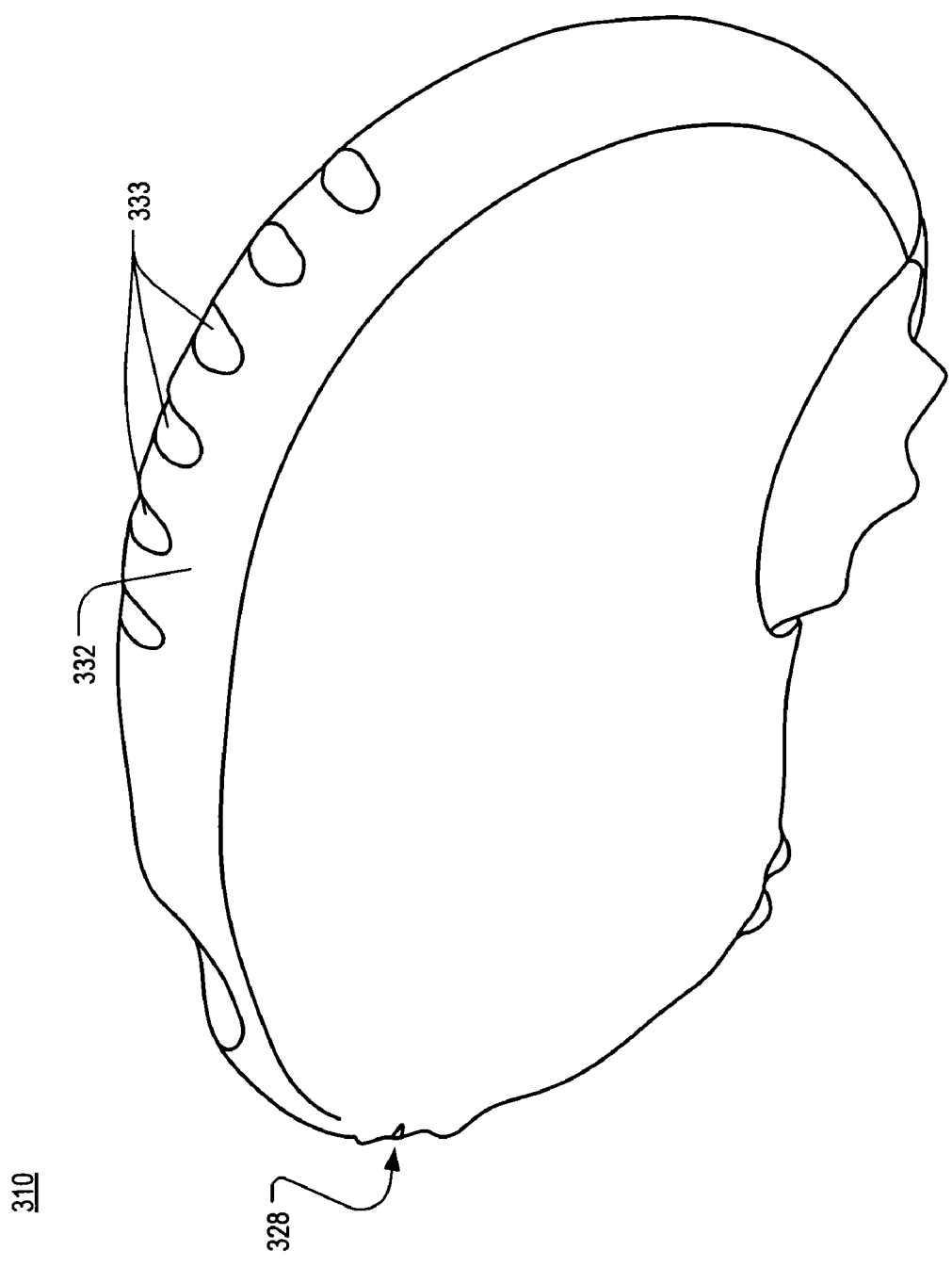
FIG. 17 is a rear perspective view of the left side of the spooled adhesive bandage dispenser of FIG. 16.
Figure 18:
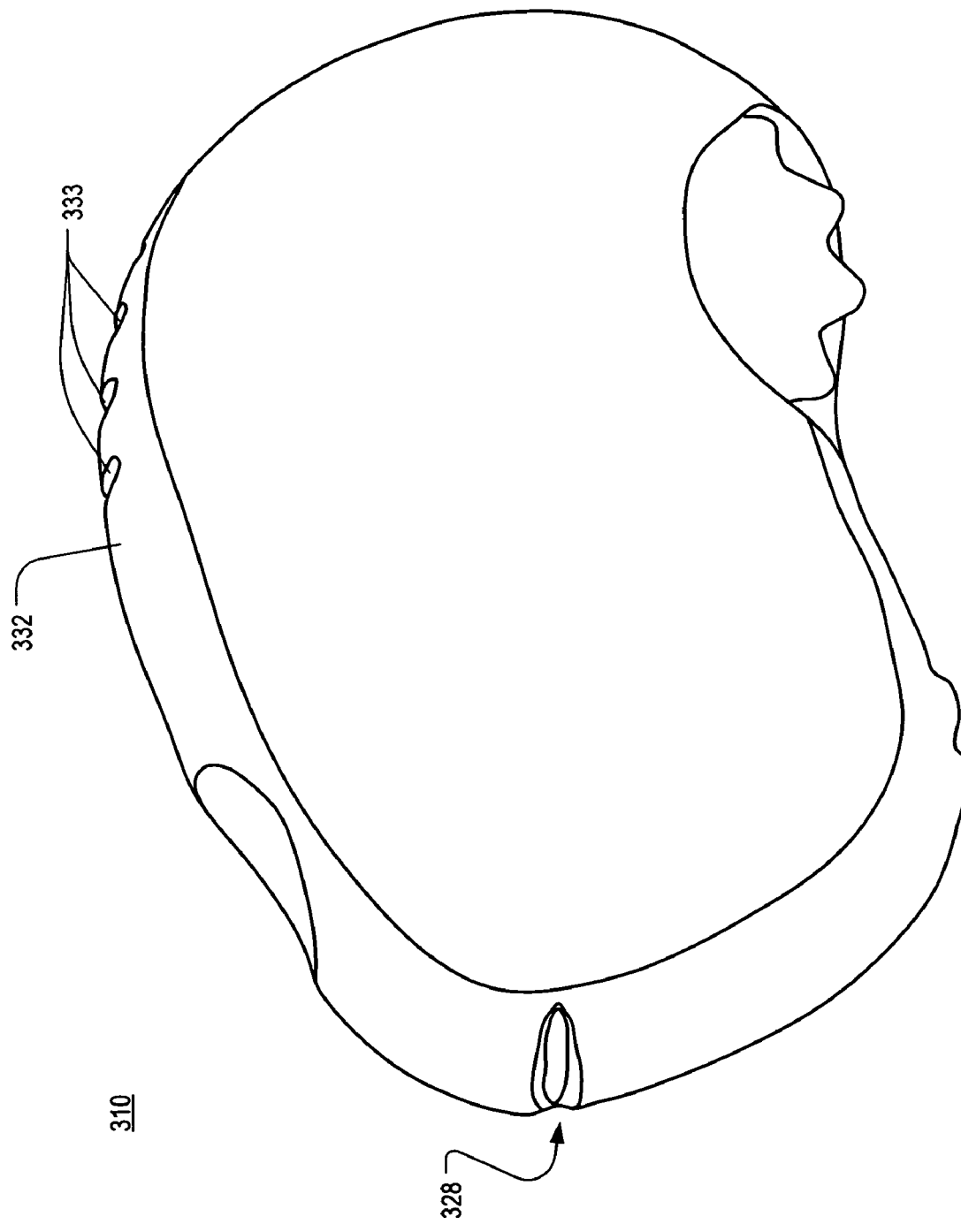
FIG. 18 is a front perspective view of the left side of the spooled adhesive bandage dispenser of FIG. 16.
Figure 19:
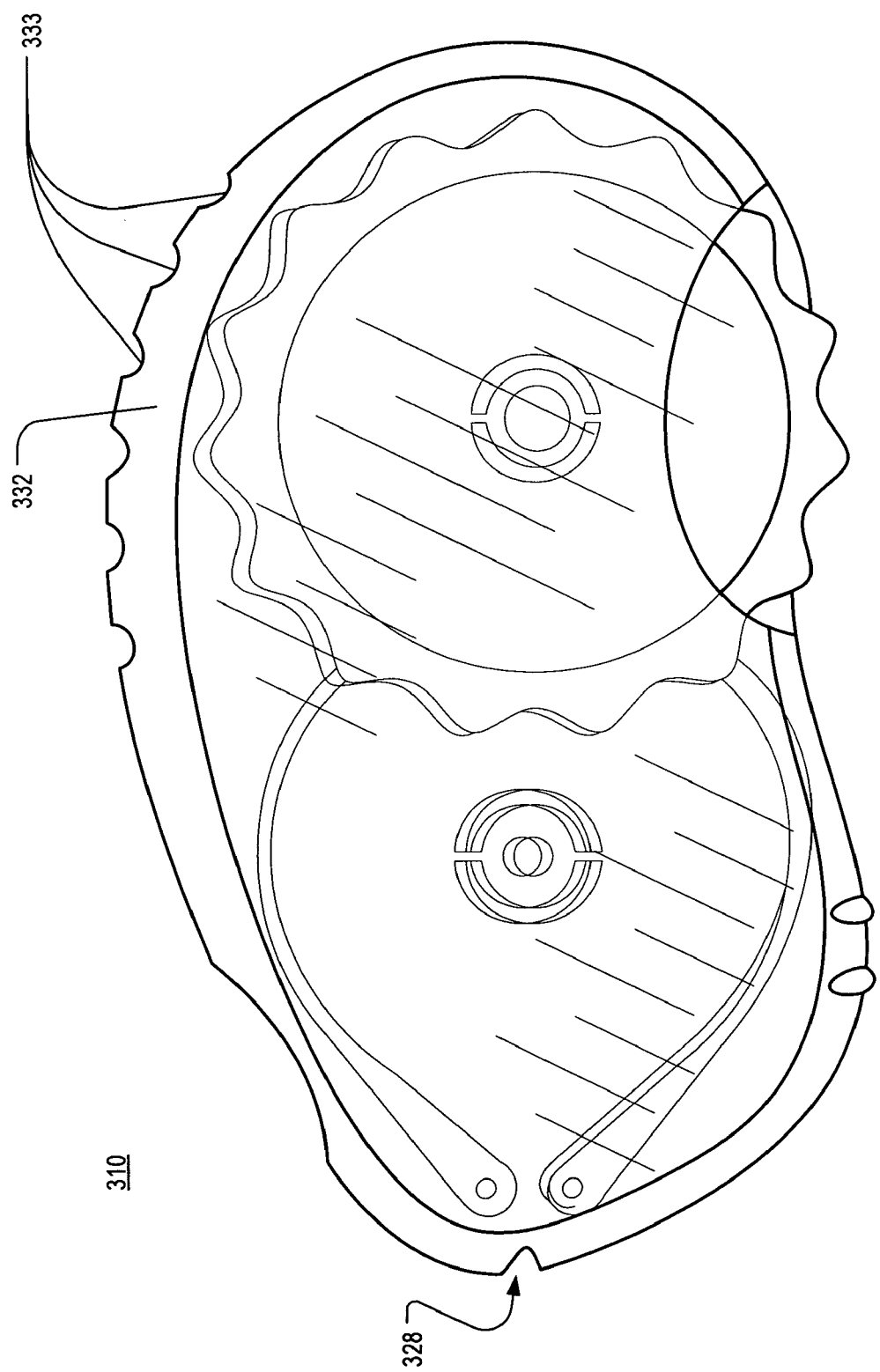
FIG. 19 is left side view of the spooled adhesive bandage dispenser of FIG. 16.
Figures 20A, 20B:
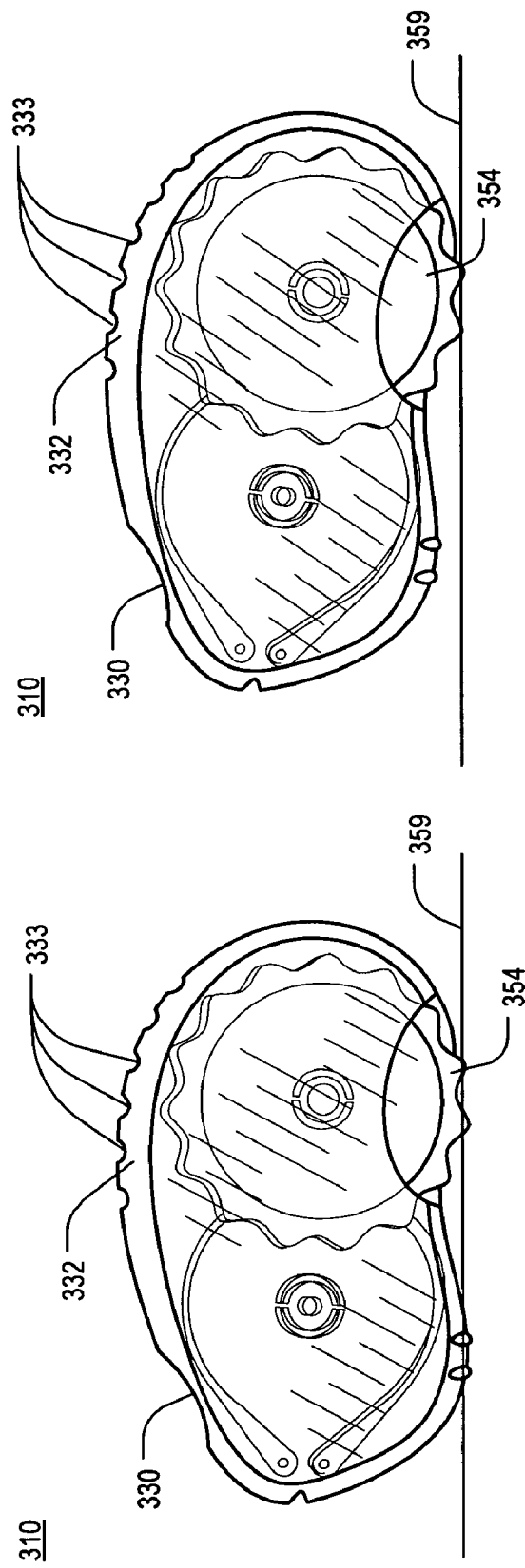
FIGS. 20A and 20B are left side views of the spooled adhesive bandage dispenser of FIG. 16, illustrating the activation of the activation wheels.

FIGS. 20A and 20B are left side views of the spooled adhesive bandage dispenser 310 of FIG. 16, illustrating the activation of the activation wheels 352,354. In operation, a user may grasp the dispenser 310, making use of the palm grip 332, indentations 333, and thumb grip 330 as desired, and at the same time cause the activation wheels 352,354 to be turned by rolling the wheels along a surface 359.

Figure 21:
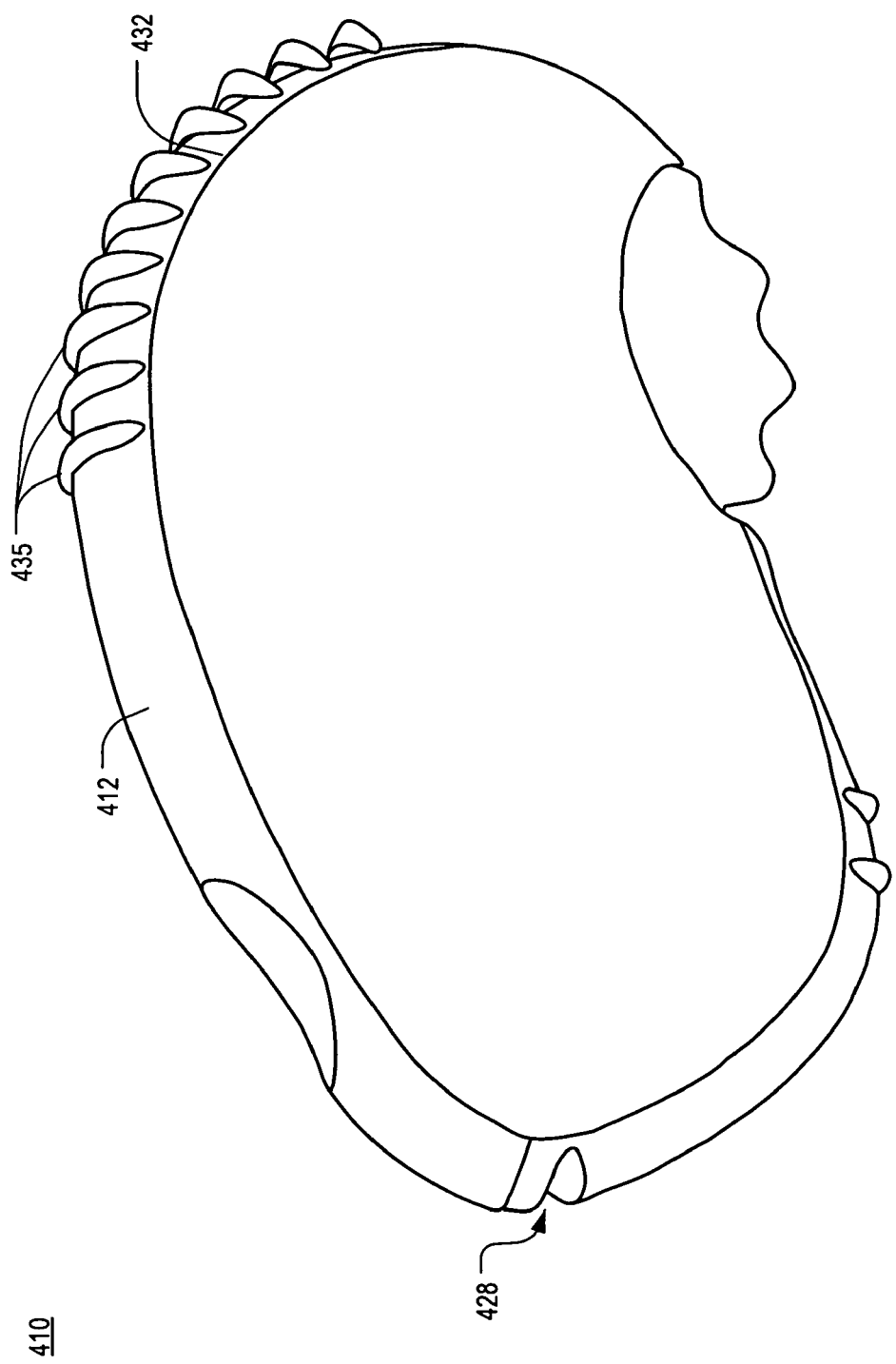
FIG. 21 is a perspective view of the left side of a spooled adhesive bandage dispenser in accordance with a fifth preferred embodiment of the present invention.

FIG. 21 is a perspective view of the left side of a spooled adhesive bandage dispenser 410 in accordance with a fifth preferred embodiment of the present invention. This dispenser 410 may be generally similar to any one of the preceding embodiments; however, one or more additional alteration is included in this fifth preferred embodiment. More particularly, the palm grip 432, which is an area along the perimeter of the case 412, at the end of the case 412 opposite the exit slot 428, that is shaped to fit in the palm of a user's hand, may include a multitude of raised ridges 435. In at least one embodiment the ridges 435 are all of uniform shape and height, are of equal distance from the preceding and following ridges 435, and are oriented perpendicular to the length of the case 412. In at least one other embodiment, however, these ridges 435 may be non-uniform in size, shape, distance from each other, or height.

Figure 22:
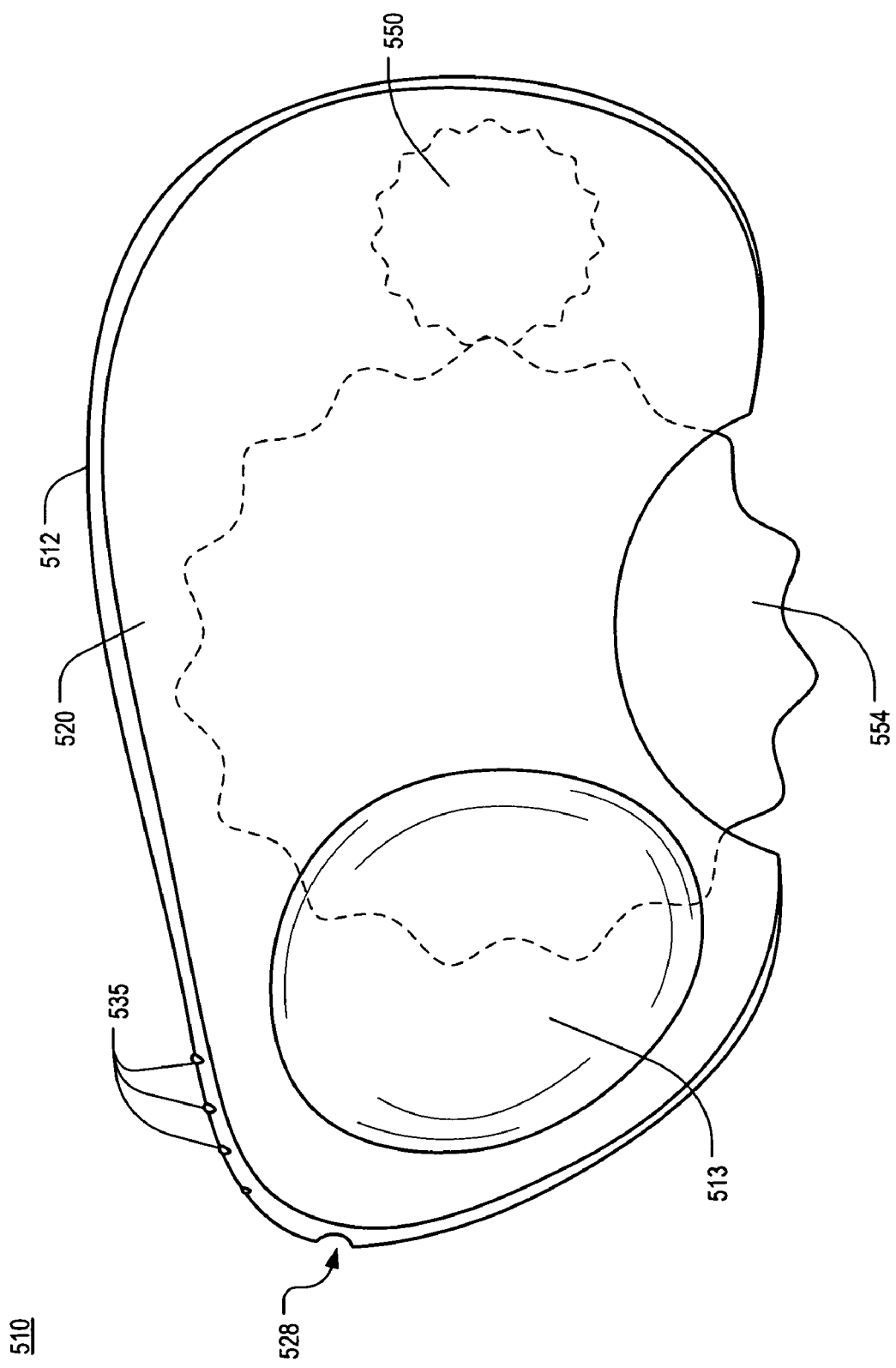
FIG. 22 is a left side view of a spooled adhesive bandage dispenser in accordance with a sixth preferred embodiment of the present invention.
Figure 23:
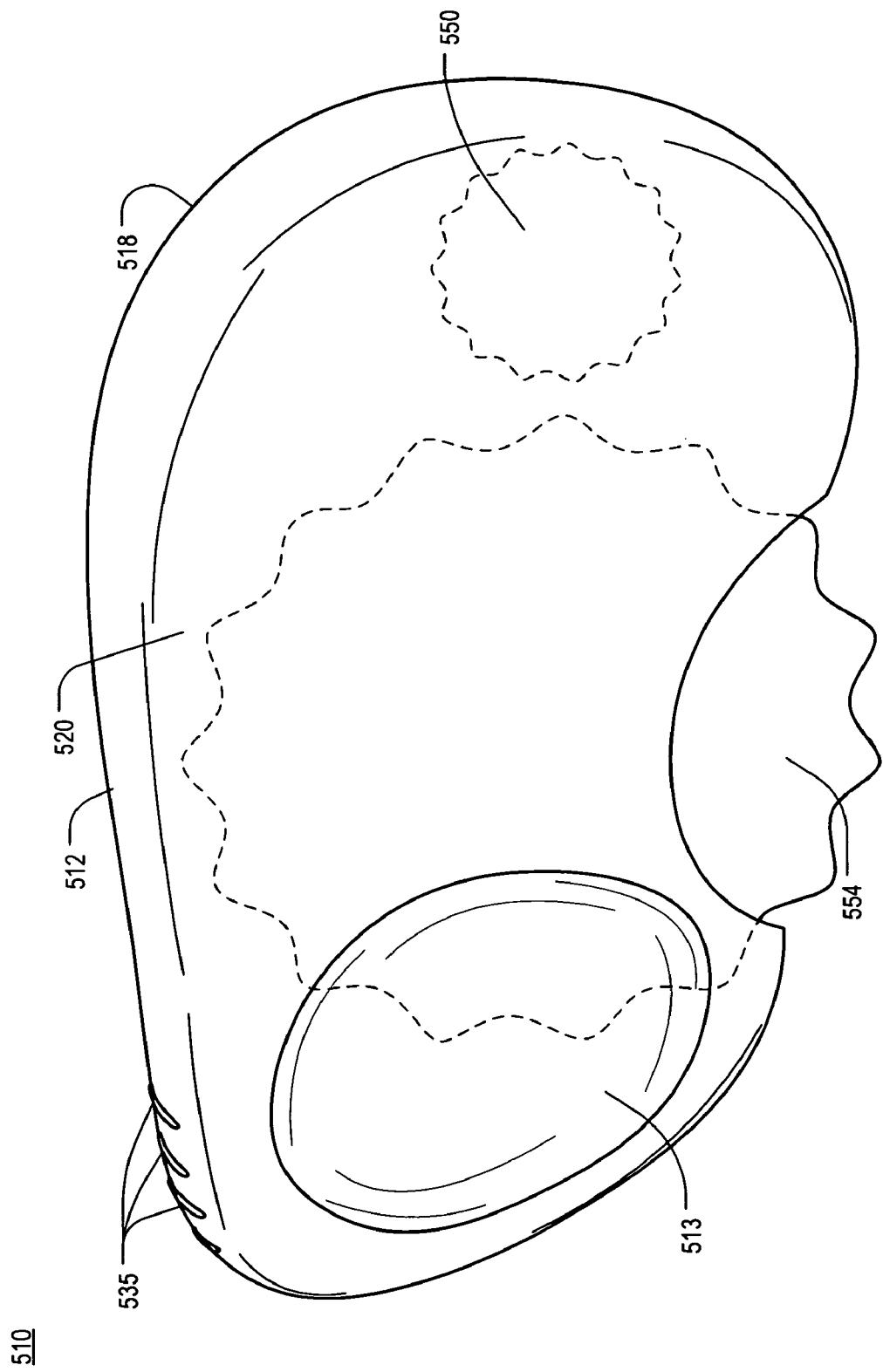
FIG. 23 is a perspective of the left side of the spooled adhesive bandage dispenser of FIG. 22.

FIGS. 22 and 23 are left side views of a spooled adhesive bandage dispenser 510 in accordance with a sixth preferred embodiment of the present invention. This dispenser 510 may be generally similar to any one of the preceding embodiments; however, one or more additional alterations may be included in this sixth preferred embodiment. More particularly, the parallel activation wheels 552,554 may be moved forward, relative to their location in previous embodiments, and coupled to a take-up reel assembly 550 such that rotating the activation wheels 552,554 in the proper rotational direction causes the waste core 576 to revolve and winds the waste strips 90,92 around the waste core 576. As the waste strips 90,92 are wound, the unseparated strip of bandage packages 82 is correspondingly unwound from the bandage roll 80. The tension placed on the packaging layers 86,88 as the waste strips 90,92 are pulled in generally opposite directions causes the first or next adhesive bandage 84 in the strip of bandage packages 82 to be gradually exposed as previously described. In at least one embodiment, the dispenser case 512 has a large, rounded dimple or depression 513 covering the front portion of one or both sides 518,520 of the case 512 such as would aid one in gripping the dispenser 510. Additionally, in at least one embodiment, and possibly in the same embodiment as the aforementioned rounded dimple 513, the front portion of the top of the case 512 has a multitude of raised ridges 535 running down the case 512 lengthwise and oriented perpendicularly to the length of the case 512 to aid one in gripping the dispenser 510.

Figure 24:
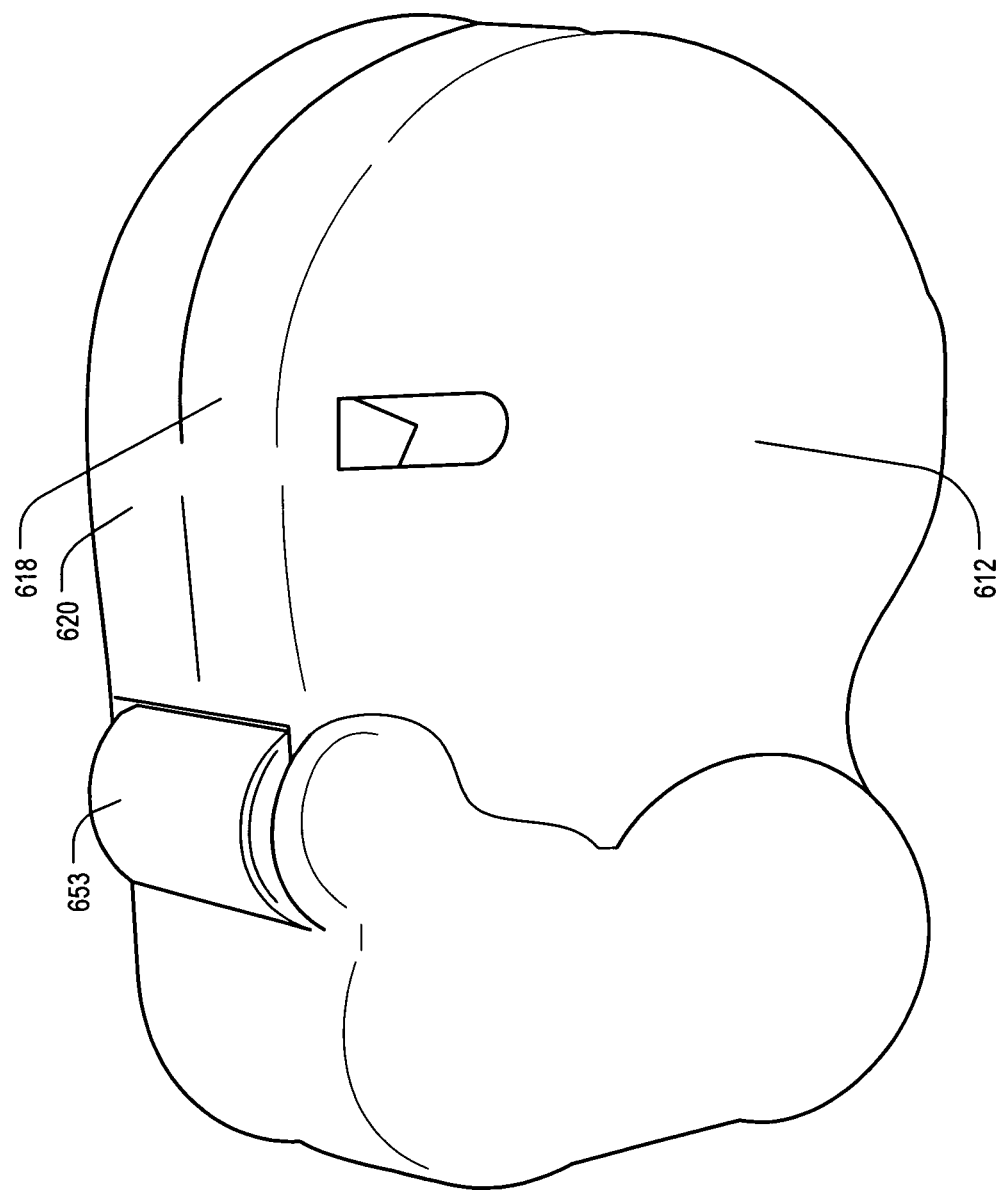
FIG. 24 is a perspective view of a spooled adhesive bandage dispenser in accordance with a seventh preferred embodiment of the present invention.
Figure 25A:
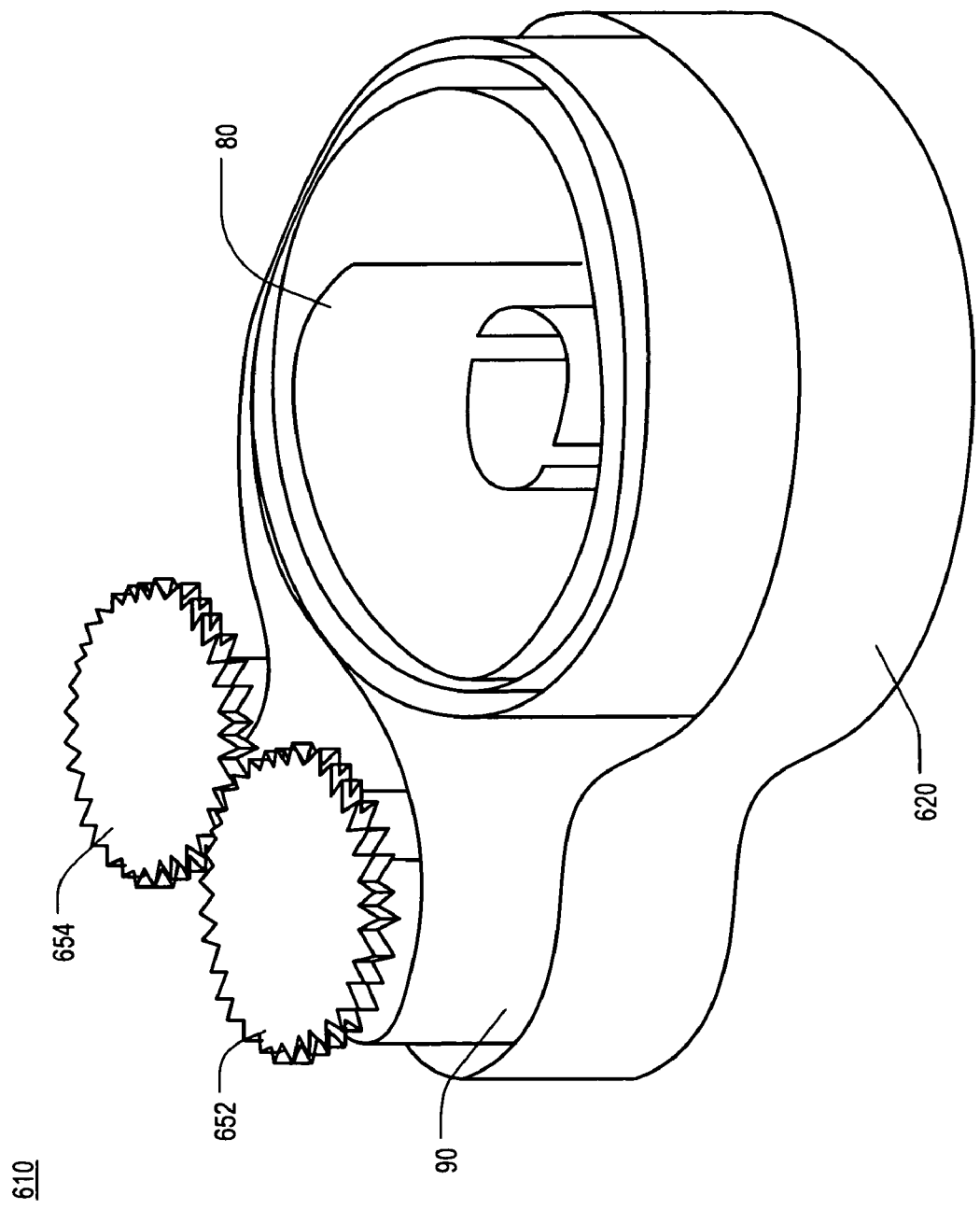
FIG. 25A is a perspective view of the spooled adhesive bandage dispenser of FIG. 24, shown with one case half and the activation wheel removed.
Figure 25C:
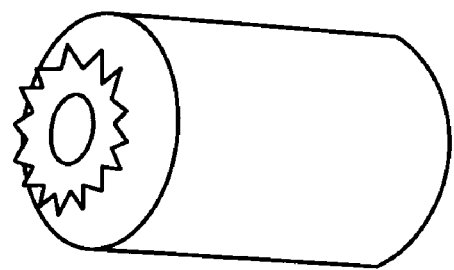
FIG. 25C is a perspective view of the activation wheel removed from the dispenser of FIG. 25A.
Figure 25B:
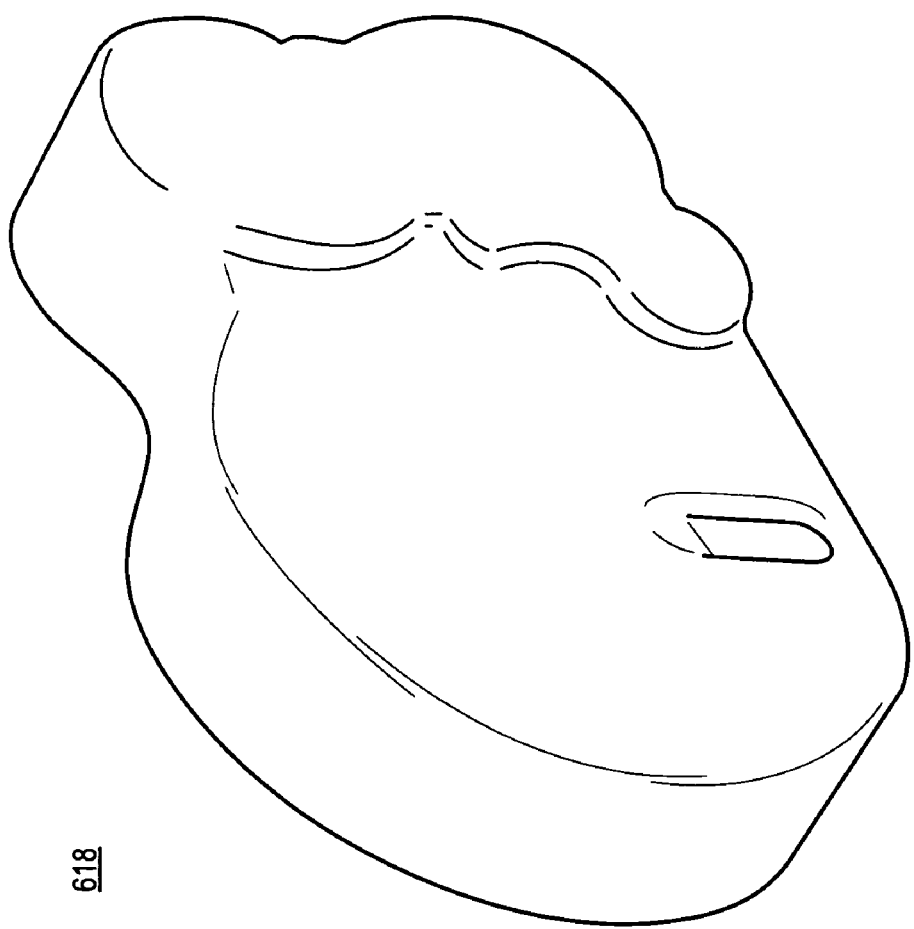
FIG. 25B is a perspective view of one case half removed from the dispenser of FIG. 25A.

FIGS. 24 and 25A-25C are perspective views of a spooled adhesive bandage dispenser 610 in accordance with a seventh preferred embodiment of the present invention. The dispenser 610 includes a case 612 made of two case halves 618,620 with an activation wheel 653 partially exposed through an opening in the top or bottom thereof. FIG. 25A is a perspective view of the spooled adhesive bandage dispenser 610 of FIG. 24, shown with one case half 618 and the activation wheel 653 removed. FIG. 25B is a perspective view of one case half 618 removed from the dispenser 610 of FIG. 25A. FIG. 25C is a perspective view of the activation wheel 653 removed from the dispenser 610 of FIG. 25A. This dispenser 610 may be generally similar to any one of the preceding embodiments; however, one or more additional alterations may be included in this seventh preferred embodiment. More particularly, the activation wheel 653 may be a small cylinder that protrudes from the bottom of the dispenser case 612 in such a way so as it may rotate unimpeded. The activation wheel 653 is coupled to a first take-up reel 654 by means of interlocking gears. The first take-up reel 654 is further coupled to a second take-up reel 652 by means of interlocking gears. As a result of this coupling, when the activation wheel 653 is activated in the proper rotational direction, the two take-up reels 652,654, which each have a leading end of a respective waste strip 90,92 wound around them, draw in the waste strips 90,92 and cause the unseparated strip of bandage packages 82 to be unwound from the bandage roll 80. The tension placed on the packaging layers 86,88 as the waste strips 90,92 are pulled in generally opposite directions causes the first or next adhesive bandage 84 in the strip of bandage packages 82 to be gradually exposed as previously described.

Figure 26:
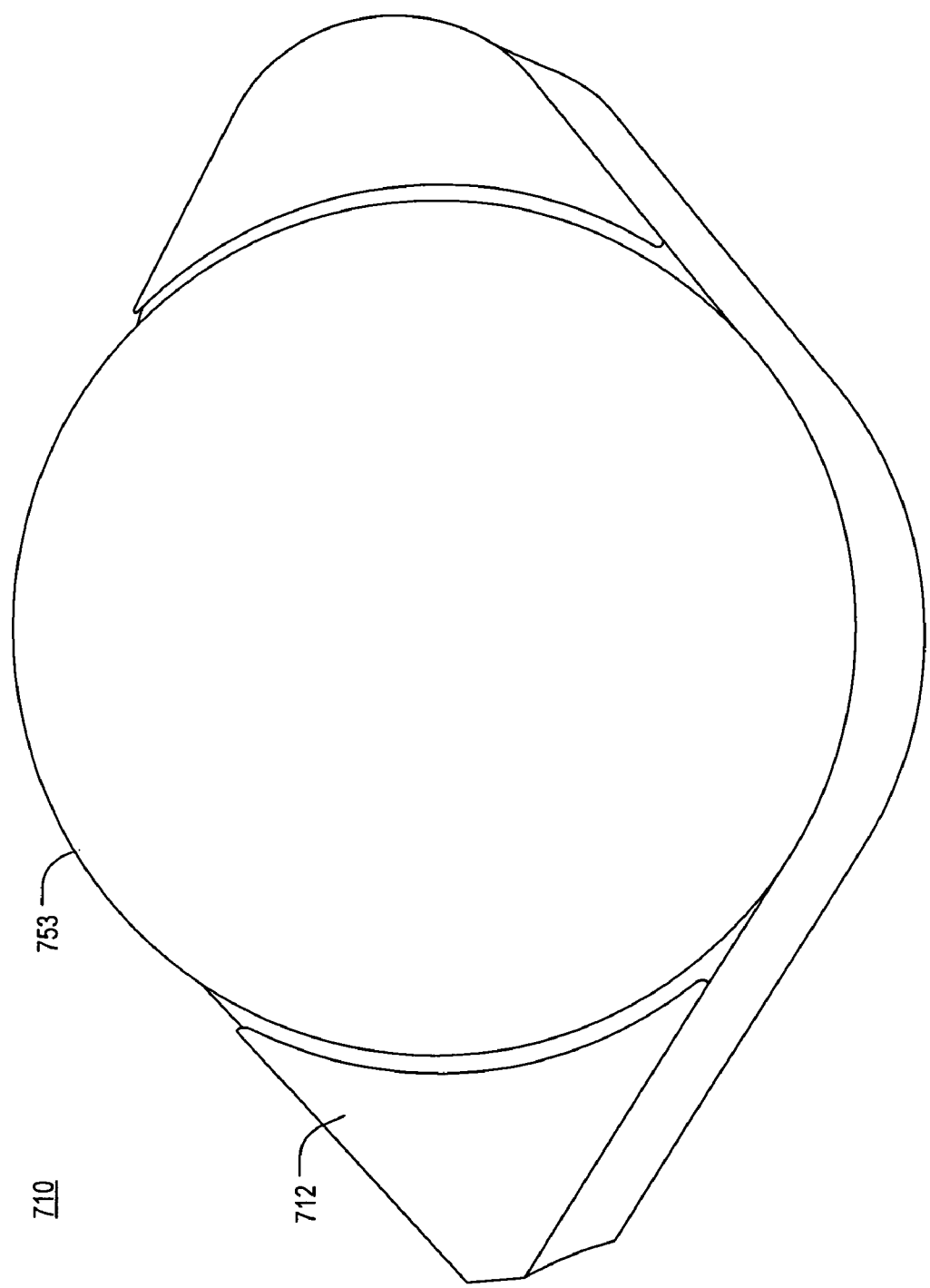
FIG. 26 is a perspective view of the side of a spooled adhesive bandage dispenser in accordance with an eighth preferred embodiment of the present invention.
Figure 27:
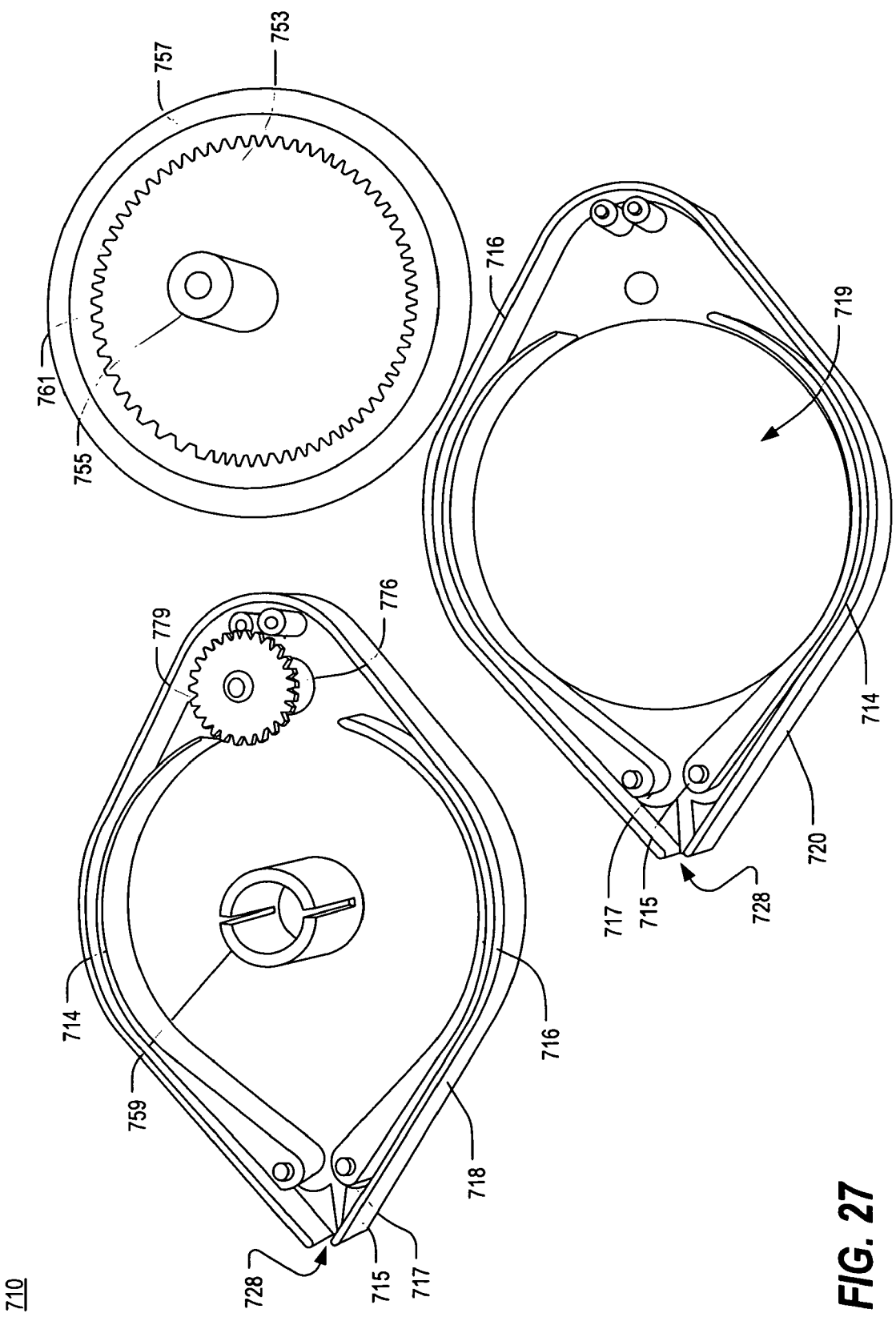
FIG. 27 is a perspective view of the elements of the spooled adhesive bandage dispenser of FIG. 26.

FIG. 26 is a perspective view of the side of a spooled adhesive bandage dispenser 710 in accordance with an eighth preferred embodiment of the present invention. As shown therein, the dispenser 710 includes a case 712 and an activation wheel 753. FIG. 27 is a perspective view of the disassembled elements of the dispenser 710 of FIG. 28. The case 710 itself is comprised of two opposing case halves: a left case half 720 and a right case half 718. The right case half 718 includes an egg shaped planar base from which extends perpendicularly a central hollowed out cylinder 759, sized for receiving a male protrusion 755 from the activation wheel 753, such that when the protrusion 755 is inserted, the activation wheel 753 is rotatably attached to the right case half 718. Rotatably attached at one end of the planar base is a waste core 776, projecting perpendicularly upward from the planar base in the same direction as the hollowed out cylinder 759, while the opposite end of the planar base features an exit slot 728 large enough to accommodate a bandage 84. The waste core 776 is topped by a circular gear 779 fixed to the waste core 776 such that when engaged by another rotating object with a geared circumference the waste core 776 will rotate. The left case half 720 includes a planar base of the same shape and size as that of the right case half 718. The left case half 720, however, features a large opening 719 in its planar base that is sized to receive the activation wheel 753. The activation wheel 753 includes the aforementioned male protrusion 755 which extends perpendicularly therefrom. On the same face of the activation wheel 753 as that from which the male protrusion 755 extends, a coaxial gear 761 is attached, formed or otherwise disposed. This gear is preferably smaller in diameter than the activation wheel and is dimensioned such that when the activation wheel 753 is rotatably attached to the right case half 718, by inserting the male protrusion 755 into the hollowed out cylinder 759, the geared circumference of the gear 761 on the activation wheel 753 will engage the gear 779 attached to the waste core 776, and thus rotation of the activation wheel 753 will cause rotation of the waste core 776.

The left case half 720 and the right case half 718 are designed such that when combined together they will form the case 712, and additionally the interior of the case will feature upper and lower waste guides 714,716. The waste guides 714,716 will each be formed when the left and right case halves 718,720 are combined together and will be shaped, spaced and dimensioned to accommodate the full diameter of a bandage roll 80 therebetween. Proximal ends 715,717 of the waste guides 714,716 are provided with generally uniform curvature and manufactured with relatively frictionless surfaces such that packaging layers 86,88 may be guided smoothly therearound.

Figure 28:
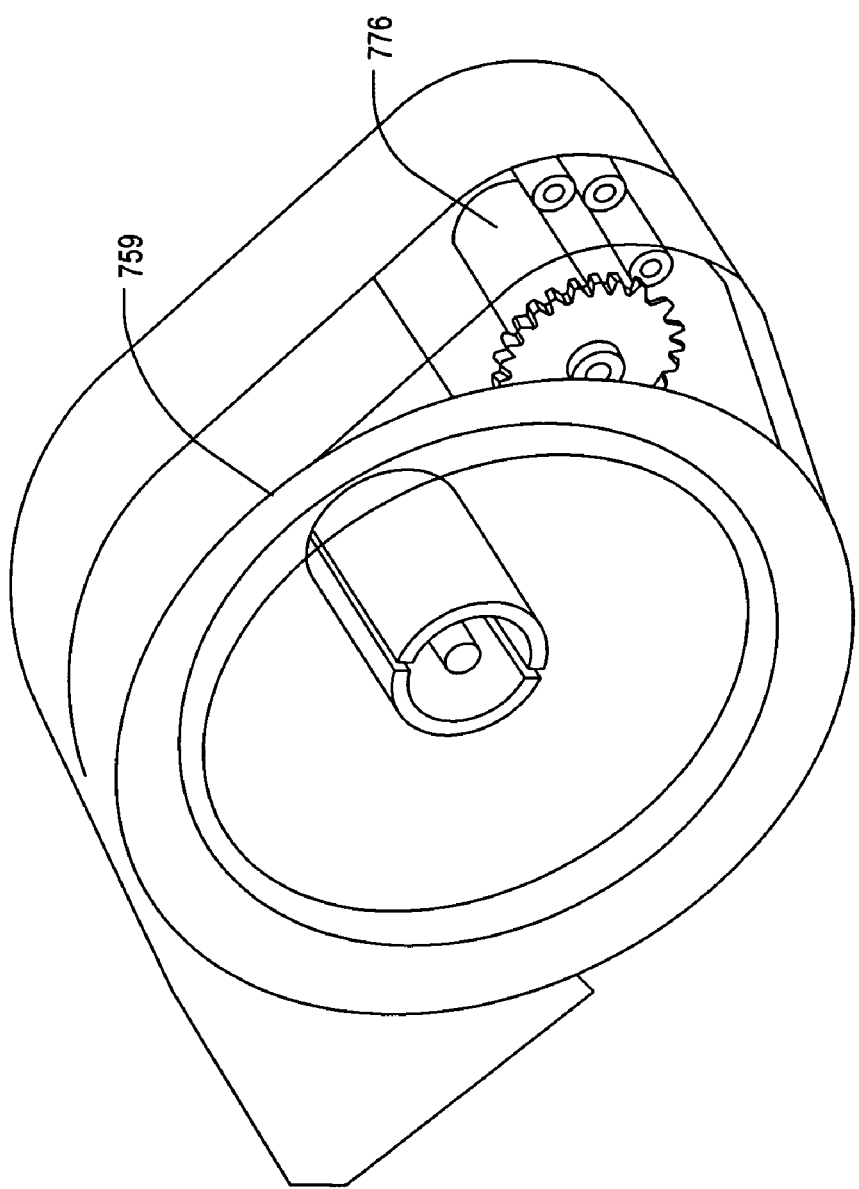
FIG. 28 is a partially transparent perspective view of the spooled adhesive bandage dispenser of FIG. 26.

FIG. 28 is a partially transparent perspective view of the spooled adhesive bandage dispenser 710 of FIG. 26. In operation, a bandage roll (not shown in FIG. 28, but which may be similar to the bandage rolls 80 described and illustrated elsewhere herein) will be arranged around the hollowed out cylinder 759 of the right case half 718. The lead end of one waste strip 90 may be guided along the upper waste guide 714 and the lead end of the other waste strip 92 may be guided along the lower waste guide 716. Both waste strips 90,92 may then be attached to the waste core 776. The left case half 720 will then be combined with the right case half 718, and the activation wheel 753 will be rotatably attached to the right case half 718, effectively holding the left and right case halves 718,720 together and forming the case 712. The activation wheel 753 may then be activated by rotation in the proper rotational direction, which will then rotate the waste core 776, winding the waste strips 90,92 around the waste core 776 and causing the waste strips 90,92, starting with their leaders, to be wound around the waste core 776. As the waste strips 90,92 are wound, the unseparated strip of bandage packages 82 is correspondingly unwound from the bandage roll 80. The tension placed on the packaging layers 86,88 as the waste strips 90,92 are pulled in generally opposite directions at the proximal ends 715,717 of the waste guides 714,716 causes the packaging layers 86,88 to unseal from each other and separate. As the rotational motion of the activation wheels 753 and waste core 776 continues, and greater lengths of the packaging layers 86,88 are separated and routed toward the waste core 776 as waste strips 90,92, the first or next adhesive bandage 84 in the strip of bandage packages 82 is gradually exposed. A leading end of the bandage 84 slides naturally between the proximal ends 715,717 of the waste guides 714, 716 and straight through the exit slot 728, where it may be retrieved by the user. The bandage 84 thus stays safely enclosed within the individual envelope of its respective bandage package 82 until forced out by the user.

Figure 29:
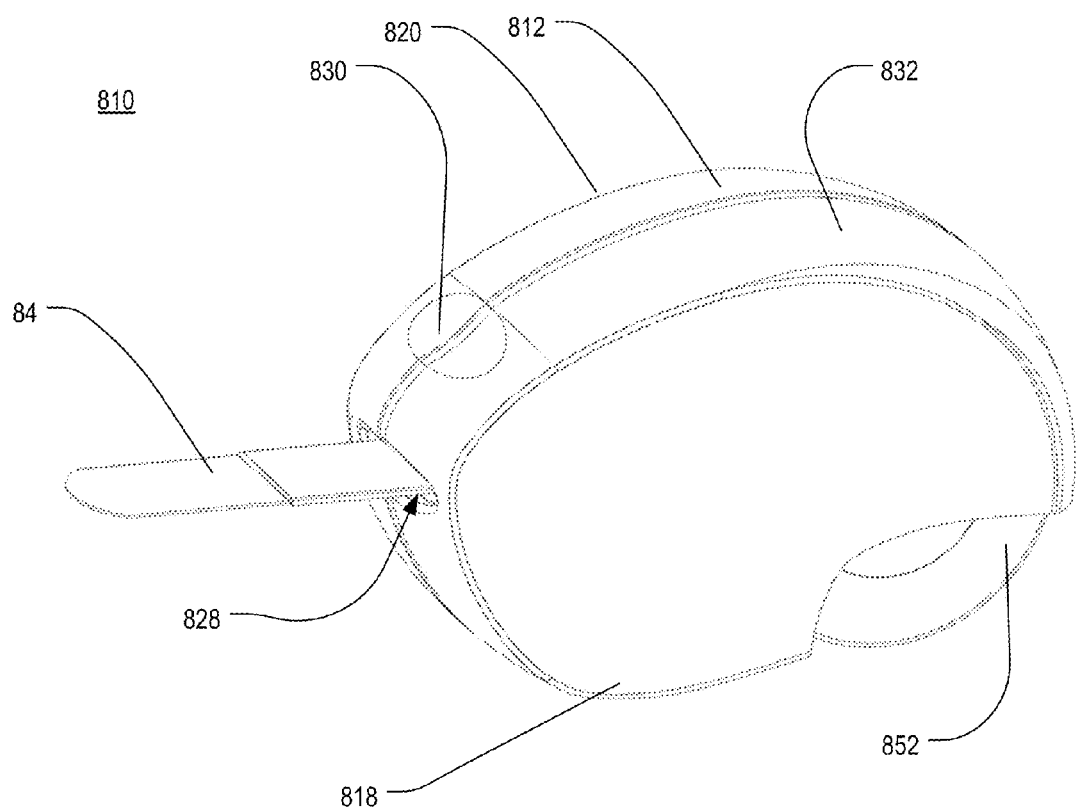
FIG. 29 is a perspective view of a spooled adhesive bandage dispenser in accordance with a ninth preferred embodiment of the present invention.
Figure 30:
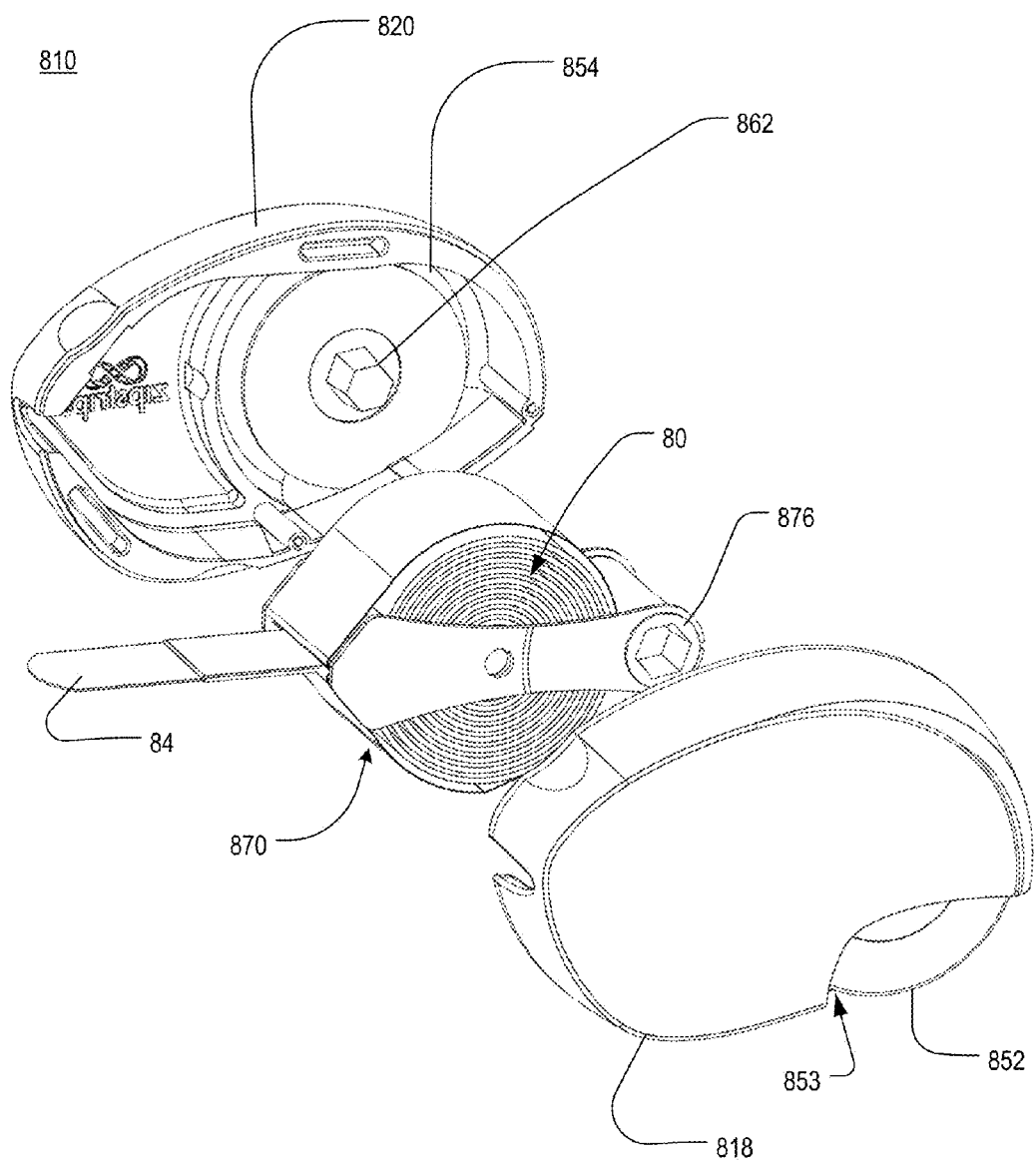
FIG. 30 is a perspective view of the spooled adhesive bandage dispenser of FIG. 29, depicting two case halves and a cartridge housed therebetween.

FIG. 29 is a perspective view of a spooled adhesive bandage dispenser 810 in accordance with a ninth preferred embodiment of the present invention. FIG. 30 is a perspective view of the spooled adhesive bandage dispenser 810 of FIG. 29, depicting two case halves 818,820 and a cartridge 870 housed therebetween. As shown therein, the dispenser 810 includes a case 812 in which are arranged a cartridge 870, a pair of activation wheels 852,854 and a plurality of routing features further described hereinbelow.

With reference to FIGS. 29 and 30, the case 812 itself, which may be formed of molded plastic, is comprised of two opposing case halves 818,820 connected together to define a housing that includes an exit slot 828, a thumb grip 830, and a palm grip 832. The palm grip 832 is an area along the perimeter of the case 812, at the end of the case 812 opposite the exit slot 828, that is shaped to fit in the palm of a user's hand, and may or may not include grooves, knobs, ridges, or the like, to be held in or make contact make with a user's palm, as further described hereinbelow, thereby making it easier and/or more comfortable for the user to hold and manipulate the dispenser 810. The case 812 and one or more of the other elements are preferably manufactured from a transparent or semi-transparent material such that the current size of a bandage roll 80 in the cartridge 870 can be seen, thereby permitting a user to gauge the number of remaining adhesive bandages 84, and so that the dispenser 810 can be monitored to ensure that waste from the bandage roll 80 is properly routed to the waste core 876 as described hereinbelow. However, in at least some embodiments, at least the case 812 is primarily manufactured from a translucent or opaque material that may or may not include a small section of transparent material through which the number of remaining adhesive bandages 84 may be gauged. Each of these elements will be described more fully hereinbelow.

Figure 31:
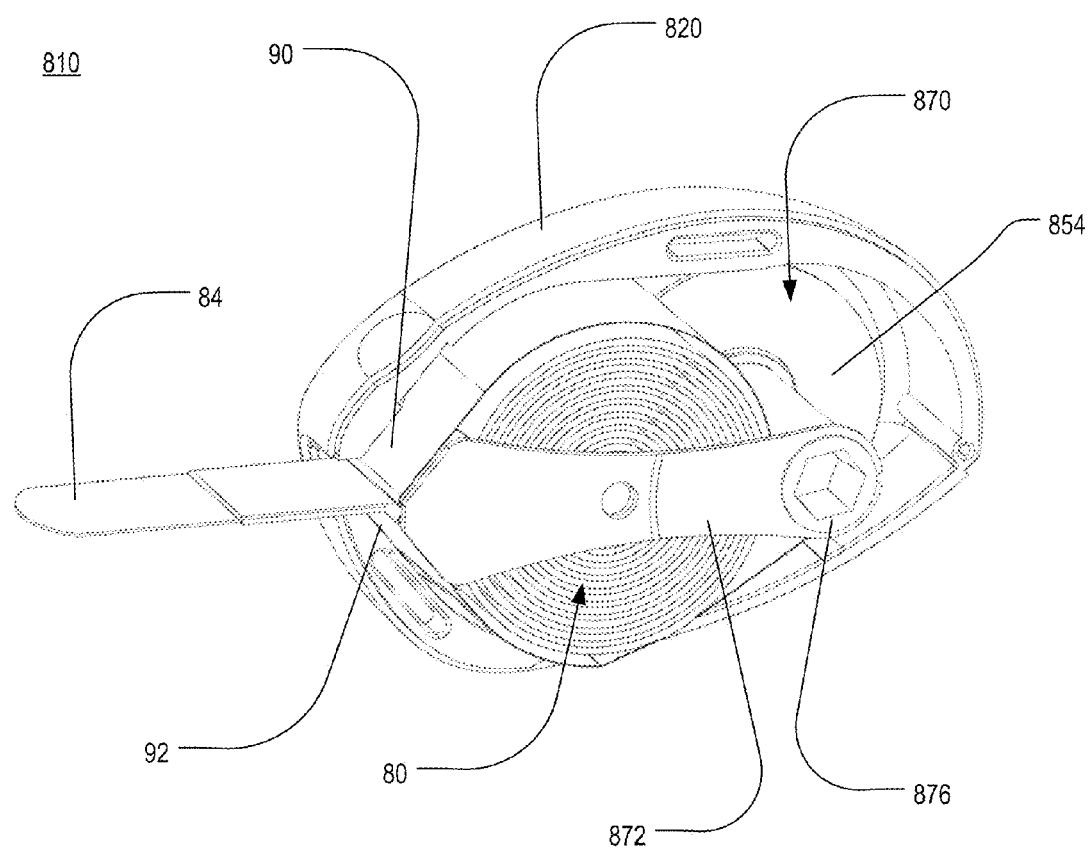
FIG. 31 is a perspective view of the right case half of the spooled adhesive bandage dispenser of FIG. 29, shown with the cartridge attached and a bandage roll installed in the cartridge.
Figure 32:
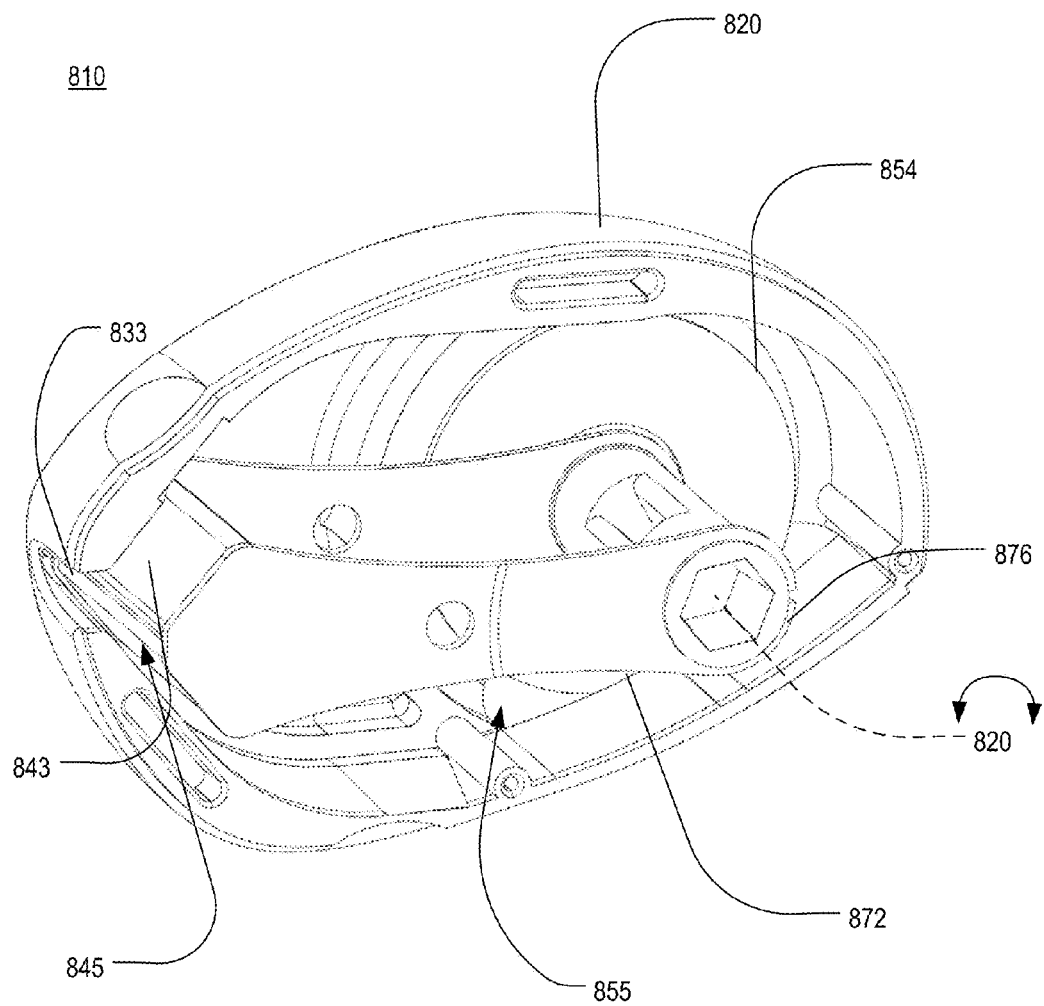
FIG. 32 is a perspective view of the right case half of the spooled adhesive bandage dispenser of FIG. 29, shown with the cartridge attached thereto and the bandage roll removed.
Figure 33:
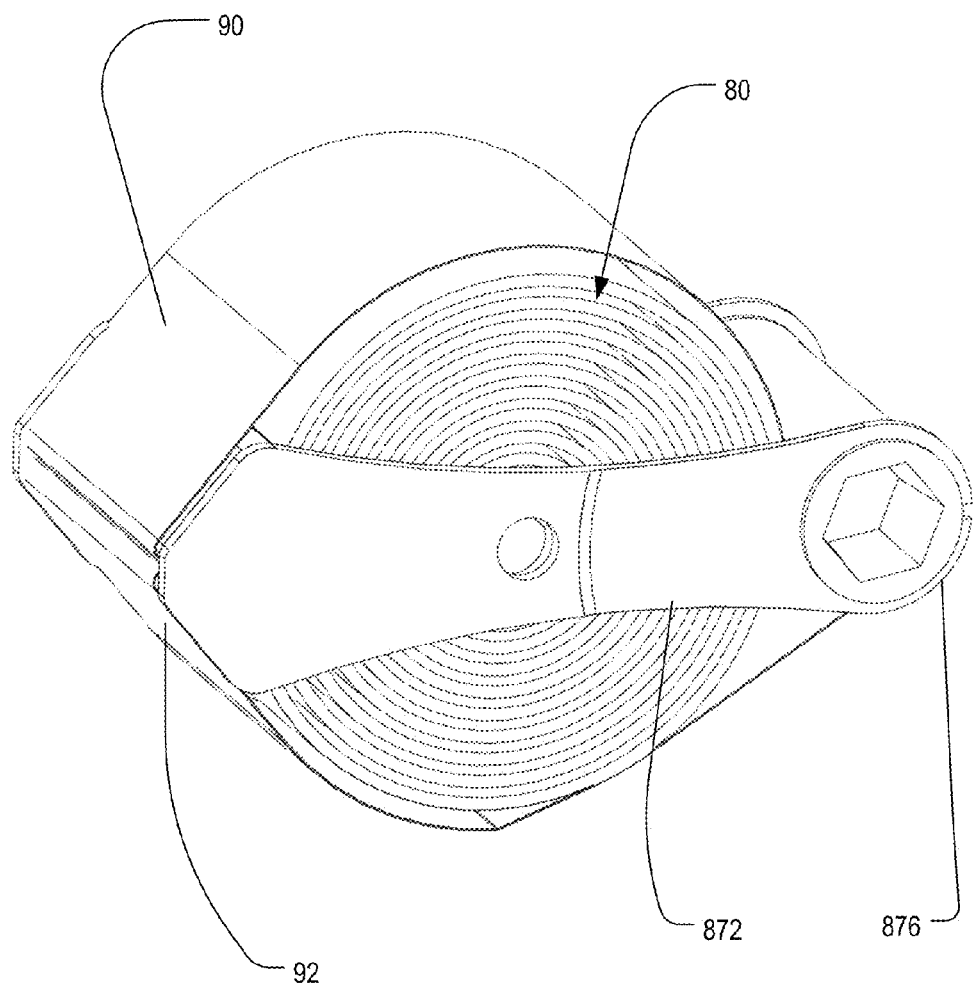
FIG. 33 is a side perspective view of the cartridge of FIG. 30.

FIG. 31 is a perspective view of the right case half 820 of the spooled adhesive bandage dispenser 810 of FIG. 29, shown with the cartridge 870 attached and a bandage roll 80 installed in the cartridge 870. FIG. 32 is a perspective view of the right case half 820 of the spooled adhesive bandage dispenser 810 of FIG. 29, shown with the cartridge 870 attached thereto and the bandage roll 80 removed. FIG. 33 is a side perspective view of the cartridge 870 of FIG. 30. The cartridge 870 includes a bandage roll 80, a frame 872 and a waste core 876. The frame 872 and the waste core 876, described further below, may each be of conventional molded plastic. The dimensions of the case 812 as well as many of the other elements of the dispenser 810 may depend upon the dimensions of the bandages 84 being dispensed therefrom. It will be appreciated that the dimensions of the dispenser 810 may be varied to accommodate the various sizes of bandages that are or may be available, such as finger size, junior size, knee size, elbow size, and the like.

The cartridge 70 includes a bandage roll 80, a frame 72 and a waste core 76. The frame 72 and the waste core 76, described further below, may each be of conventional molded plastic. In at least one embodiment, the bandage roll 80 comprises a relatively long strip of individual adhesive bandage packages, connected end-to-end, that is loosely spooled with no center core to create a roll. In at least one other embodiment, the bandage roll 80 comprises a similar strip of individual adhesive bandage packages that is spooled around a central core to create a roll. Each bandage package includes an individual adhesive bandage 84 sandwiched between two layers of packaging such that the bandage 84 is encased in a sealed envelope. It will be appreciated that bandages of any type or construction may be dispensed according to one or more preferred embodiments of the present invention, including plastic, fabric, clear, waterproof, and the like. Each packaging layer is a continuous strip of material that is sealed to the other layer, such as by heat sealing, around the perimeter of each bandage 84 and at the ends of each bandage 84. The properties of the material are such that the bandage envelopes thus created are able to maintain the bandages 84 in a sterile environment until opened for use as described below. One material suitable for use in one or more preferred embodiments of the present invention is a conventional paper wrapper, but it will be appreciated that other materials capable of keeping the bandages 84 sterile may likewise be used.

The packaging layers are further capable of being unsealed, thereby exposing the bandages 84 contained therebetween one-by-one, without being torn or broken, thereby permitting the unsealed layers to be collected as waste strips 90,92 on the waste core 876. A leading end of each waste strip 90,92 is wrapped around or otherwise connected to the waste core 876 such that rotation of the waste core 876 causes the waste strips 90,92 to be wound therearound. Notably, each waste strip 90,92 is wound around the waste core 876 in the same direction, such that rotation in the proper direction causes both waste strips 90,92 to be wound simultaneously. In at least some embodiments, the portion of each waste strip 90,92 near its leading end defines a leader, and may be formed from the same material used for the remainder of the packaging layers or from a different material.

The waste core 876 is a structure defining an exterior winding surface and means for coupling the core 876 to the activation wheels 852,854 as described below. Together, the waste core 876 and activation wheels 852,854 may, in at least some embodiments, define a take-up reel assembly. Further, in at least some embodiments, the exterior winding surface is non-circular, or more particularly, is oblong or includes flat surfaces in addition to curved surfaces. In addition to providing some advantage in the winding operation, such a non-circular shape may more conveniently be used on the interior of the core 876 as well; such a shape makes it easier to couple the core 876 to a correspondingly-shaped structure on the activation wheels 852,854, further described hereinbelow, because the non-circular shape prevents rotation, i.e., free-wheeling, of the core 876 without corresponding rotation of the activation wheels 852,854.

With particular reference to FIG. 32, the cartridge frame 872 includes a nosepiece 833 at the front of the case 812, adjacent the exit slot 828. The nosepiece 833 includes a pair of planar flanges 843,845 angled away from the exit slot 828 and arranged in generally opposed relationship. The cartridge frame 872 is adapted to support and position the nosepiece 833 within the case 812. The planar flanges 843,845 are shaped, spaced and dimensioned to accommodate the full diameter of the bandage roll 80 within the case 812. The nosepiece 833 is configured in such a way as to guide bandages 84 out of the exit slot 828 and waste strips 90,92 toward the waste core 876. More specifically, the nosepiece 833 is positioned such that the waste strips 90,92 are routed more smoothly to the waste core 876 and occupy less space within the case 812. An additional gap created between proximate edges of the two planar flanges 843,845 may help in more smoothly guiding each unwrapped bandage 84 through the exit slot 828.

The activation wheels 852,854, which are parallel to each other but spaced apart, are each rotatably attached to a respective case half 818,820 such that their rotation relative to the case 812 occurs about a common axis of rotation 822. A further coupling, such as in the form of an extension 862 having a distal end forming a male coupling for engagement with a female coupling formed by the interior of the waste core 876. In such an arrangement, each extension 862 may, in at least some embodiments, have a cross-sectional shape that matches that of the interior of the waste core 876, and in particular that matches the oblong or other non-circularly-shaped interior of the waste core 876, described above. The cross-sectional shape of the extension 862 may vary. As shown in FIG. 30, the extension 862 has a generally hexagonal cross-sectional shape to match the interior hexagonal shape of the waste core 876. As noted previously, the non-circular shape of the male and female couplings prevents rotation, i.e., free-wheeling, of the core 876 without corresponding rotation of the activation wheels 852,854.

It will be appreciated that, in at least some embodiments, the design and construction of the waste core 876 may be varied without departing from the scope of the present invention. For example, the waste core 876 may be constructed from a biodegradable material, such as cardboard, rather than molded plastic. The waste core may be cylindrical and provided with a central bore through which an axle or the like may be inserted fully therethrough, rather than interlocking with the extensions on the activation wheels 852,854 as described herein. Two separate waste cores may likewise be utilized, one for each waste strip 90,92.

Though generally disposed in the interior of the case 812, each activation wheel 852,854 is partially exposed to the exterior via a respective opening 853,855 in the bottom of the case 812. Any of a variety of features may be applied to the perimeter or rim of each activation wheel 852,854 to permit a user to easily rotate the activation wheels 852,854 by manipulating one or both of the rims thereof. In one embodiment, a rubber or plastic band is wrapped around the rim to provide this function, but in some embodiments, grooves, knobs, ridges, or the like, some of which are further described and illustrated herein, may be formed or otherwise provided along the rim, or the rim may be provided with a textured surface or formed or otherwise manufactured from a material providing an increased level of friction.

Figure 34A:
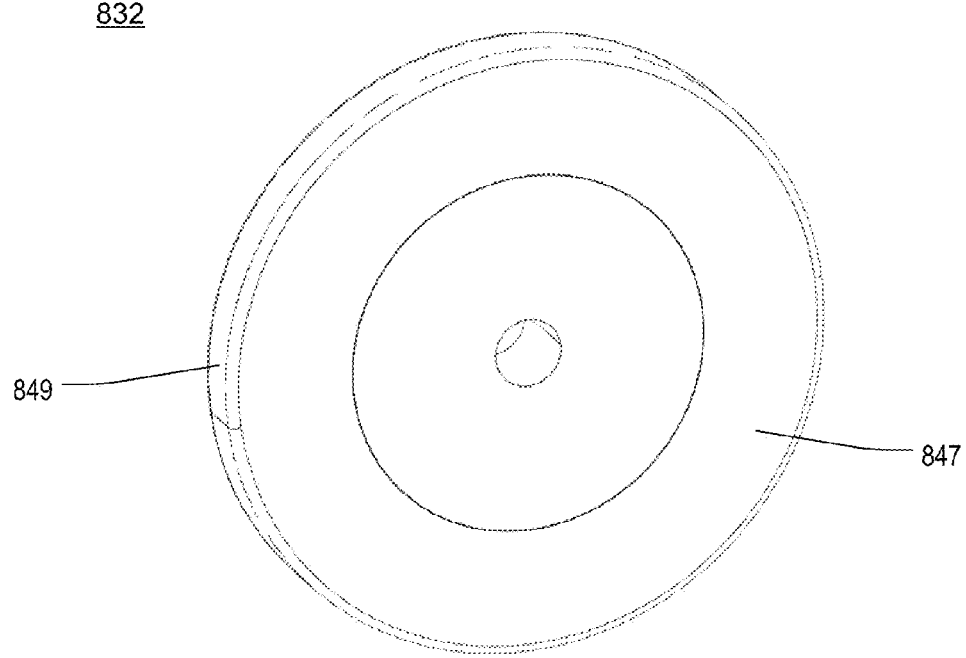
FIG. 34A is an outside perspective view of one of the activation wheels of FIG. 29.
Figure 34B:
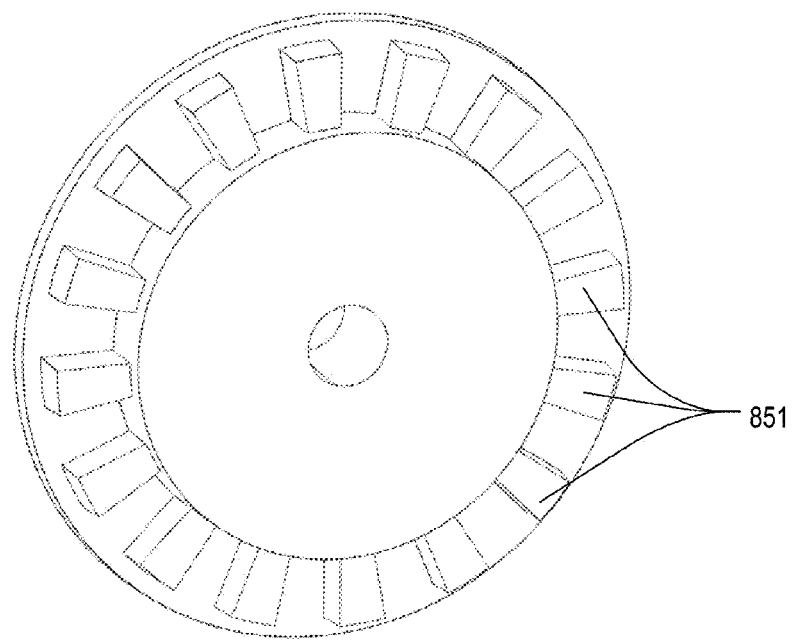
FIG. 34B is an inside perspective view of the hub of FIG. 34A with the tire removed.

One particular wheel arrangement is illustrated in FIGS. 34A and 34B, wherein FIG. 34A is an outside perspective view of one of the activation wheels 832 of FIG. 29 and FIG. 34B is an inside perspective view of the hub 847 of FIG. 34A with the tire 849 removed. More particularly, each wheel 832,834 utilizes a central hub 847, from which the extension 862 protrudes (not shown in FIGS. 34A and 34B), having a friction material in the form of a rubber or plastic "tire" 849 wrapped around the periphery thereof. The tire 849 may be molded around the hub 847 in a co-molding or overmolding process. To aid in this process, the hub 847 may include a plurality of structures 851 for interfacing with and retaining the tire material during the manufacturing process.

The cartridge 870 is installed in the case 812 such that the frame 872 is mounted in its intended position in the case 812 and the waste core 876 is coupled to the extensions on the interior sides of the activation wheels 852,854. In operation, a user may grasp the dispenser 810, making use of the palm grip 832 and thumb grip 830 as desired, and at the same time cause the activation wheels 852,854 to be turned. Such action, if applied to the activation wheels 852,854 in the proper rotational direction, causes the waste strips 90,92, starting with their leaders, to be wound around the waste core 876. As the waste strips 90,92 are wound, the unseparated strip of bandage packages is correspondingly unwound from the bandage roll 80. The tension placed on the packaging layers as the waste strips 90,92 are pulled in generally opposite directions causes the packaging layers to unseal from each other and separate. As the rotational motion of the activation wheels 852,854 and waste core 876 continues, and greater lengths of the packaging layers are separated and routed toward the waste core 876 as waste strips 90,92, the first or next adhesive bandage 84 in the strip of bandage packages 82 is gradually exposed. A leading end of this bandage 84 slides naturally through the exit slot 828, where it may be retrieved by the user. The bandage 84 thus stays safely enclosed within its respective bandage package 82 until forced out by the user.

In the illustrated embodiment, the cartridge 870 is of a replaceable type, wherein the entire cartridge 870, including the frame 872, the waste core 876 and all of the waste strips 90,92 wrapped therearound, may be removed and replaced by a new cartridge 870. In other embodiments, the frame remains but the waste core 876, including the waste strips 90,92, is removed and a new bandage roll 80 and waste core 876 are installed. In at least one commercial application of either such embodiment, the dispenser 810 is made available to consumers in a state in which it is preloaded with a full roll 80, while in at least one other such commercial application each dispenser 810 comes unloaded but ready for loading by the user. In either such commercial application, replacement cartridges 870 or rolls 80 may be sold or otherwise offered together with each dispenser 810, or such replacement cartridges 812 or rolls 80 may be sold or otherwise offered separately. In at least some other embodiments, neither the cartridge 870 nor the bandage roll 80 is individually replaceable, and the entire dispenser 810 must be replaced once the roll 80 is spent.

Based on the foregoing information, it is readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to its preferred embodiment, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof. Although specific terms are employed herein, they are used in a generic and descriptive sense only and not for the purpose of limitation.

What is claimed is:

1. A spooled adhesive bandage dispenser, comprising:
   (a) a case;
   (b) a bandage roll disposed at least partially in the case and having a plurality of bandages connected together in end-to-end relationship;
   (c) an activation wheel, at least partially exposed outside the case, for causing a bandage to be forced out of the case;
   (d) a waste core disposed at least partially within the case and in operative connection with the activation wheel, wherein the activation wheel is configured to receive and wind at least one waste strip from the bandage roll as an exposed bandage is forced out of the case; and
   (e) at least two waste guides, disposed adjacent and partially surrounding the bandage roll, for guiding waste strips from the bandage roll to the waste core as an exposed bandage is forced out of the case.

2. The spooled adhesive bandage dispenser of claim 1, further comprising a take-up reel assembly, disposed at least partially within the case, for receiving and winding at least one waste strip from the bandage roll as an exposed bandage is forced out of the case.

3. The spooled adhesive bandage dispenser of claim 1, wherein each waste guide defines a waste channel within the case, thereby providing an uninterrupted path to the waste core for waste strips unwound from the bandage roll.

4. The spooled adhesive bandage dispenser of claim 1, further comprising a nosepiece disposed generally between the bandage roll and an exit slot of the case through bandages exit from the case, wherein the nosepiece is adapted for guiding waste strips from the bandage roll to the waste core as an exposed bandage is forced out of the case.

5. The spooled adhesive bandage dispenser of claim 1, wherein the bandage roll is contained on a replaceable cartridge.

6. The spooled adhesive bandage dispenser of claim 1, wherein the case is made of molded plastic.

7. The spooled adhesive bandage dispenser of claim 1, wherein the waste core is made from a biodegradable material.

8. The spooled adhesive bandage dispenser of claim 1, wherein the activation wheel includes two spaced apart activation wheels, each wheel being rotatably attached to a side of the case such that their rotation relative to the case occurs about a common axis of rotation.

9. The spooled adhesive bandage dispenser of claim 1, wherein the activation wheel includes a gripping band arranged about the perimeter thereof.

10. The spooled adhesive bandage dispenser of claim 1, further comprising a latch to facilitate opening the case.

11. A spooled adhesive bandage dispenser, comprising:
    (a) a case;
    (b) a bandage roll disposed at least partially in the case; and
    (c) a take-up reel assembly, disposed at least partially within the case, for receiving and winding at least one waste strip from the bandage roll as an exposed bandage is forced out of the case,
    (d) wherein the take-up reel assembly includes at least two waste guides, disposed adjacent and partially surrounding the bandage roll, for guiding waste strips from the bandage roll to the waste core as an exposed bandage is force out of the case.

12. The spooled adhesive bandage dispenser of claim 11, wherein the take-up reel assembly includes at least one activation wheel at least partially exposed outside the case, each of the at least one wheel being rotatably attached to a side of the case such that its rotation relative to the case occurs about a common axis of rotation, wherein rotation of the at least one activation wheel forces an exposed bandage out of the case.

13. The spooled adhesive bandage dispenser of claim 12, wherein the take-up reel assembly includes a waste core disposed at least partially within the case and in operative connection with the activation wheel, wherein the activation wheel is configured to receive and wind at least one waste strip from the bandage roll as an exposed bandage is forced out of the case.

14. The spooled adhesive bandage dispenser of claim 11, wherein the bandage roll is contained on a replaceable cartridge.

15. The spooled adhesive bandage dispenser of claim 11, wherein the case is made of molded plastic.

16. A spooled adhesive bandage dispenser, comprising:
   (a) a case;
   (b) a bandage roll disposed at least partially in the case;
   (c) at least one activation wheel at least partially exposed outside the case, each of the at least one activation wheel being rotatably attached to a side of the case such that its rotation relative to the case occurs about a common axis of rotation; and
   (c) at least two waste guides, disposed adjacent and partially surrounding the bandage roll, for guiding waste strips from the bandage roll as an exposed bandage is forced out of the case;
   (d) wherein rotation of the at least one activation wheel forces an exposed bandage out of the case.

17. The spooled adhesive bandage dispenser of claim 16, wherein the bandage roll is contained on a replaceable cartridge.

* * * * *